United States Patent
Held et al.

(10) Patent No.: US 11,976,276 B2
(45) Date of Patent: *May 7, 2024

(54) METHOD FOR RECOVERING TWO OR MORE GENES, OR GENE PRODUCTS, ENCODING AN IMMUNORECEPTOR

(71) Applicant: Memo Therapeutics AG, Schlieren (CH)

(72) Inventors: Martin Held, Zürich (CH); Christoph Esslinger, Zürich (CH)

(73) Assignee: Memo Therapeutics AG, Schlieren (CH)

( * ) Notice: Subject to any disclaimer, the term of this patent is extended or adjusted under 35 U.S.C. 154(b) by 84 days.

This patent is subject to a terminal disclaimer.

(21) Appl. No.: 17/520,330

(22) Filed: Nov. 5, 2021

(65) Prior Publication Data
US 2022/0127599 A1    Apr. 28, 2022

Related U.S. Application Data

(63) Continuation of application No. 15/118,676, filed as application No. PCT/EP2015/053135 on Feb. 13, 2015, now Pat. No. 11,312,952.

(30) Foreign Application Priority Data

Feb. 14, 2014    (GB) ..................... 1402591

(51) Int. Cl.
| | | |
|---|---|---|
| *C12N 15/10* | (2006.01) | |
| *C07K 16/00* | (2006.01) | |
| *C12Q 1/6806* | (2018.01) | |
| *C12Q 1/686* | (2018.01) | |
| *G01N 33/50* | (2006.01) | |
| *G01N 33/68* | (2006.01) | |

(52) U.S. Cl.
CPC .......... *C12N 15/1082* (2013.01); *C07K 16/00* (2013.01); *C07K 16/005* (2013.01); *C12Q 1/6806* (2013.01); *C12Q 1/686* (2013.01); *G01N 33/5023* (2013.01); *G01N 33/5047* (2013.01); *G01N 33/6845* (2013.01); *G01N 33/6854* (2013.01)

(58) Field of Classification Search
CPC .. C12N 15/1082; C07K 16/00; C12Q 1/6806; C12Q 1/686; C12Q 2521/107; C12Q 2563/149; C12Q 2563/159
See application file for complete search history.

(56) References Cited

U.S. PATENT DOCUMENTS

| | | | | |
|---|---|---|---|---|
| 2010/0136544 A1* | 6/2010 | Agresti | ................ | B01J 13/0052 |
| | | | | 435/287.2 |
| 2010/0310558 A1* | 12/2010 | Oleksiewicz | ........ | C07K 16/005 |
| | | | | 506/14 |
| 2011/0059556 A1* | 3/2011 | Strey | ................ | G01N 33/54326 |
| | | | | 422/503 |
| 2011/0129855 A1 | 6/2011 | Pedersen et al. | | |
| 2011/0275063 A1* | 11/2011 | Weitz | ................ | G01N 33/5436 |
| | | | | 435/7.1 |
| 2012/0301919 A1* | 11/2012 | Yang | ...................... | C12N 15/67 |
| | | | | 435/189 |

FOREIGN PATENT DOCUMENTS

| | | |
|---|---|---|
| EP | 1 516 929 A2 | 3/2005 |
| WO | WO 02/097122 A1 | 12/2002 |
| WO | WO 2013/188872 A1 | 12/2013 |
| WO | WO 2015/121434 A1 | 8/2015 |

OTHER PUBLICATIONS

Kurosawa et al. (BMC biotechnology 11.1 (2011): 39; 8 pages) (Year: 2011).*
Dekosky et al. (Nature biotechnology 31.2 (2013): 166-169) (Year: 2013).*
International Search Report and Written Opinion was dated Jun. 2, 2012 for International Application No. PCT/EP2015/053135, which was filed on Feb. 13, 2015 and published as WO/2015/121434 on Aug. 20, 2015 (Inventor—Martin Held et al.; Applicant—Memo Therapeutics AG) (5 pages).
Dekosky, B.J., et al., "High-Throughput Sequencing of the Paired Human Immunoglobulin Heavy and Light Chain Repertoire," *Nature Biotechnology* 31(2):166-169, Springer Nature Limited, Germany (2013).
Kurosawa, N., et al., "Target-Selective Homologous Recombination Cloning for High-Throughput Generation of Monoclonal Antibodies From Single Plasma Cells," *BMC Biotechnology* 11(39):1-8, BioMed Central, United Kingdom (2011).
Bernasconi, N.L., et al., "Maintenance of Serological Memory by Polyclonal Activation of Human Memory B Cells," *Science* 298:2199-2202, American Association for the Advancement of Science, United States (2002).
Boulianne, G.L., et al., "Production of Functional Chimaeric Mouse/Human Antibody," *Nature* 312:643-646, Nature Publishing Group, England (1984).
Card, K.F., et al., "A Soluble Single-Chain T-Cell Receptor IL-2 Fusion Protein Retains MHC-Restricted Peptide Specificity and IL-2 Bioactivity," Cancer Immunology, *Immunotherapy* 53(4):345-357, Springer Verlag, Germany (2004).

(Continued)

*Primary Examiner* — Sahana S Kaup
(74) *Attorney, Agent, or Firm* — Sterne, Kessler, Goldstein & Fox P.L.L.C.

(57) ABSTRACT

The present invention is related to a method for recovering two or more genes, or gene products, or cDNAs, encoding for an immunoreceptor having two or more subunits, which two or more genes, or gene products, are comprised in a given source cell. The invention is further related to a method of creating a library of expressor cells, in which library each cell is capable of expressing two or more genes, or gene products, encoding for the subunits of the immunoreceptor. The invention is further related to a method of screening a library of expressor cells as created according to the above method, for one cell that expresses an immunoreceptor that has specificity for a given target molecule.

18 Claims, 8 Drawing Sheets

Specification includes a Sequence Listing.

(56) References Cited

OTHER PUBLICATIONS

Diehl, F., et al., "BEAMing: Single-Molecule PCR on Microparticles in Water-in-Oil Emulsions," *Nature Methods* 3(7):551-559, Supplementary Material, Nature Pub. Group, United States (2006).

Dull T., et al., "A Third-Generation Lentivirus Vector with a Conditional Packaging System," *Journal of Virology* 72(11):8463-8471, American Society for Microbiology, Washington. (1998).

Embleton, M.J., et al., "In-Cell PCR from mRNA: Amplifying and Linking the Rearranged Immunoglobulin Heavy and Light Chain V-Genes within Single Cells," *Nucleic Acids Research* 20(15):3831-3837, Oxford University Press, London(1992).

Gibson, D.G., et al., "Enzymatic Assembly of DNA Molecules up to Several Hundred Kilobases," *Nature Methods* 6(5):343-345, Supplementary Material, Nature Pub. Group, United States (May 2009).

Gomez-Herreros, F., et al., "TFIIS is Required for the Balanced Expression of the Genes Encoding Ribosomal Components Under Transcriptional Stress," *Nucleic Acids Research* 40(14):6508-6519, Oxford University Press, England (2012).

Martinez, C.J., et al., "A Microfluidic Approach to Encapsulate Living Cells in Uniform Alginate Hydrogel Microparticles," *Macromolecular Bioscience* 12(7):946-951, Wiley-VCH, Germany (2012).

Mcheyzer-Williams, M.G. and Ahmed, R., "B Cell Memory and the Long-Lived Plasma Cell," *Current Opinion in Immunology* 11(2):172-179, Elsevier, Netherlands (1999).

Meijer, PJ. et al., "Isolation of Human Antibody Repertoires With Preservation of the Natural Heavy and Light Chain Pairing," *J Mol Biol* 358(3):764-772, Elsevier, Netherlands (2006).

Morrison, S.L., et al., "Chimeric Human Antibody Molecules: Mouse Antigen-binding Domains with Human Constant Region Domains," *Proceedings of the National Academy of Sciences USA* 81(21):6851-6855, National Academy of Sciences, United States (1984).

Prüße, U., et al., "New Process (Jet Cutting Method) for the Production of Spherical Beads from Highly Viscous Polymer Solutions," *Chemical Engineering & Technology* 21(1):29-33, Wiley-VCH Verlag GmbH, Gerrmany (1998).

Serp, D., et al., "Characterization of an Encapsulation Device for the Production of Monodisperse Alginate Beads for Cell Immobilization," *Biotechnology and Bioengineering* 70(1):41-53, John Wiley & Sons, Inc., United States (2000).

Szymczak, A.L., et al., "Correction of Multi-Gene Deficiency in Vivo using a Single 'Self-Cleaving' 2A Peptide-Based Retroviral Vector," *Nature Biotechnology* 22(5):589-594, Supplemental Material, Nature America Publishing, United States (2004).

Wardemann, H., et al., "Predominant Autoantibody Production by Early Human B Cell Precursors," *Science* 301(5638):1374-1377, American Association for the Advancement of Science, United States (2003).

Chen, W., et al., "BEAMing and Droplet Digital PCR Analysis of Mutant IDH1 mRNA in Glioma Patient Serum and Cerebrospinal Fluid Extracellular Vesicles," *Molecular Therapy—Nucleic Acids* 2(7): e109, the American Society of Gene & Cell Therapy, United States (2013).

McDaniel, J.R., et al., "Ultra-high-throughput sequencing of the immune receptor repertoire from millions of lymphocytes," *Nature Protocols* 11(3): 429-442, Nature America, Inc. (2016).

* cited by examiner

A)  B)

SEQUENCE LISTING

<160> NUMBER OF SEQ ID NOS: 68

<210> SEQ ID NO 1
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH First PCR Sense 5' L-VH3

<400> SEQUENCE: 1
cccagatggg tcctgtccca ggtgcag                                          27

<210> SEQ ID NO 2
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH First PCR Sense 5' L-VH1

<400> SEQUENCE: 2
acaggtgccc actcccaggt gcag                                          24

<210> SEQ ID NO 3
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primers Ig-variable heavy chain 5'
      SPVH1

<400> SEQUENCE: 3
acaggtgccc actcccaggt gcag                                          24

<210> SEQ ID NO 4
<211> LENGTH: 51
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: oePCR Primers CK2

<400> SEQUENCE: 4
accgcctcca ccggcggccg cttattaaca ctctcccctg ttgaagctct t            51

<210> SEQ ID NO 5
<211> LENGTH: 37
<212> TYPE: DNA
<213> ORGANISM: Artificial Sequence
<220> FEATURE:
<223> OTHER INFORMATION: Synethic construct
<220> FEATURE:
<221> NAME/KEY: misc_feature
<223> OTHER INFORMATION: oePCR Primers CK1

<400> SEQUENCE: 5
atatatatgc ggccgcttaa cactctcccc tgttgaa                            37

<210> SEQ ID NO 6
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk Second PCR Sense 5' Pan Vk

<400> SEQUENCE: 6
atgacccagw ctccabycwc cctg                                          24

<210> SEQ ID NO 7
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk First PCR Sense 5' L Vk1/2

<400> SEQUENCE: 7
atgaggstcc cygctcagct gctgg                                         25

<210> SEQ ID NO 8
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  First PCR Sense  5' L Vk4

<400> SEQUENCE: 8
atttctctgt tgctctggat ctctg                                   25

<210> SEQ ID NO 9
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: nPCR 5' primer

<400> SEQUENCE: 9
attttttttg cgcgctgt                                           18

<210> SEQ ID NO 10
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH First PCR Sense 5' L-VH5

<400> SEQUENCE: 10
caaggagtct gttccgaggt gcag                                    24

<210> SEQ ID NO 11
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl First PCR  Antisense 3' Cl

<400> SEQUENCE: 11
caccagtgtg gccttgttgg cttg                                    24

<210> SEQ ID NO 12
<211> LENGTH: 27
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH First PCR Sense 5' L-VH4/6

<400> SEQUENCE: 12
cccagatggg tcctgtccca ggtgcag                                 27

<210> SEQ ID NO 13
<211> LENGTH: 28
<212> TYPE: DNA

```
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl Second PCR  Antisense 3' XhoI Cl

<400> SEQUENCE: 13
ctcctcactc gagggygga acagagtg                                          28

<210> SEQ ID NO 14
<211> LENGTH: 28
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  First PCR Sense  5' L Vk3

<400> SEQUENCE: 14
ctcttcctcc tgctactctg gctcccag                                         28

<210> SEQ ID NO 15
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH Second PCR  Sense 5' AgeI VH1/5

<400> SEQUENCE: 15
ctgcaaccgg tgtacattcc gaggtgcagc tggtgcag                              38

<210> SEQ ID NO 16
<211> LENGTH: 40
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  Specific PCR  Sense  5' AgeI Vk 2-24

<400> SEQUENCE: 16
ctgcaaccgg tgtacatggg gatattgtga tgacccagac                            40

<210> SEQ ID NO 17
<211> LENGTH: 40
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  Specific PCR  Sense  5' AgeI Vk 2-28

<400> SEQUENCE: 17
ctgcaaccgg tgtacatggg gatattgtga tgactcagtc                            40

<210> SEQ ID NO 18
<211> LENGTH: 40
<212> TYPE: DNA
<213> ORGANISM: Artificial Sequence
<220> FEATURE:
<223> OTHER INFORMATION: Synthetic construct
<220> FEATURE:
```

```
<221> NAME/KEY: misc_feature
<223> OTHER INFORMATION: Igk  Specific PCR  Sense  5' AgeI Vk 3-15

<400> SEQUENCE: 18
ctgcaaccgg tgtacattca gaaatagtga tgacgcagtc                              40

<210> SEQ ID NO 19
<211> LENGTH: 40
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH Second PCR  Sense 5' AgeI VH4-34

<400> SEQUENCE: 19
ctgcaaccgg tgtacattcc caggtgcagc tacagcagtg                              40

<210> SEQ ID NO 20
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH Second PCR  Sense 5' AgeI VH4

<400> SEQUENCE: 20
ctgcaaccgg tgtacattcc caggtgcagc tgcaggag                                38

<210> SEQ ID NO 21
<211> LENGTH: 40
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  Specific PCR  Sense  5' AgeI Vk 4-1

<400> SEQUENCE: 21
ctgcaaccgg tgtacattcg gacatcgtga tgacccagtc                              40

<210> SEQ ID NO 22
<211> LENGTH: 40
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  Specific PCR  Sense  5' AgeI Vk 1-5

<400> SEQUENCE: 22
ctgcaaccgg tgtacattct gacatccaga tgacccagtc                              40

<210> SEQ ID NO 23
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH Second PCR  Sense 5' AgeI VH3

<400> SEQUENCE: 23
```
ctgcaaccgg tgtacattct gaggtgcagc tggtggag        38

<210> SEQ ID NO 24
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH Second PCR  Sense 5' AgeI VH3-23

<400> SEQUENCE: 24
ctgcaaccgg tgtacattct gaggtgcagc tgttggag        38

<210> SEQ ID NO 25
<211> LENGTH: 40
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  Specific PCR  Sense  5' AgeI Vk 1D-43

<400> SEQUENCE: 25
ctgcaaccgg tgtacattgt gccatccgga tgacccagtc        40

<210> SEQ ID NO 26
<211> LENGTH: 40
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primers Overlap extension PCR 5' BSSH2
      VH434

<400> SEQUENCE: 26
ctgcagcgcg cgtacattcc caggtgcagc tacagcagtg        40

<210> SEQ ID NO 27
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primers Overlap extension PCR 5' BSSH2
      VH4

<400> SEQUENCE: 27
ctgcagcgcg cgtacattcc caggtgcagc tgcaggag        38

<210> SEQ ID NO 28
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primers Overlap extension PCR 5' BSSH2
      VH1/5

<400> SEQUENCE: 28
ctgcagcgcg cgtacattcc gaggtgcagc tggtgcag                                    38

<210> SEQ ID NO 29
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primers Overlap extension PCR 5' BSSH2
      VH3

<400> SEQUENCE: 29
ctgcagcgcg cgtacattct gaggtgcagc tggtggag                                    38

<210> SEQ ID NO 30
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primers Overlap extension PCR 5' BSSH2
      VH323

<400> SEQUENCE: 30
ctgcagcgcg cgtacattct gaggtgcagc tgttggag                                    38

<210> SEQ ID NO 31
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl Second PCR  Sense 5' AgeI Vl7/8

<400> SEQUENCE: 31
ctgctaccgg ttccaattcy cagrctgtgg tgacycag                                    38

<210> SEQ ID NO 32
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl Second PCR  Sense 5' AgeI Vl2

<400> SEQUENCE: 32
ctgctaccgg ttcctgggcc cagtctgccc tgactcag                                    38

<210> SEQ ID NO 33
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl Second PCR  Sense 5' AgeI Vl1

<400> SEQUENCE: 33
ctgctaccgg ttcctgggcc cagtctgtgc tgackcag                                    38

<210> SEQ ID NO 34
<211> LENGTH: 37
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl Second PCR  Sense 5' AgeI V14/5

<400> SEQUENCE: 34
ctgctaccgg ttctctctcs cagcytgtgc tgactca                                37

<210> SEQ ID NO 35
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl Second PCR  Sense 5' AgeI Vl3

<400> SEQUENCE: 35
ctgctaccgg ttctgtgacc tcctatgagc tgacwcag                               38

<210> SEQ ID NO 36
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl Second PCR  Sense 5' AgeI Vl6

<400> SEQUENCE: 36
ctgctaccgg ttcttgggcc aattttatgc tgactcag                               38

<210> SEQ ID NO 37
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: oePCR Primers CH

<400> SEQUENCE: 37
gacsgatggg cccttggtgg                                                   20

<210> SEQ ID NO 38
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl First PCR  Sense 5' L Vl8

<400> SEQUENCE: 38
gagtggattc tcagactgtg gtg                                               23

<210> SEQ ID NO 39
<211> LENGTH: 30
<212> TYPE: DNA

<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  Specific PCR  Antisense 3' BsiWI Jk5

<400> SEQUENCE: 39
gccaccgtac gtttaatctc cagtcgtgtc                                    30

<210> SEQ ID NO 40
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  Second PCR  Antisense 3' BsiWI Jk 3

<400> SEQUENCE: 40
gccaccgtac gtttgatatc cactttggtc                                    30

<210> SEQ ID NO 41
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  Specific PCR  Antisense 3' BsiWI Jkl1/2/4

<400> SEQUENCE: 41
gccaccgtac gtttgatytc caccttggtc                                    30

<210> SEQ ID NO 42
<211> LENGTH: 26
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Ig-variable kappa light chain linker primer 5
    XbaI Vl

<400> SEQUENCE: 42
gccgcgcagt gcgaatatct agatgt                                        26

<210> SEQ ID NO 43
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl First PCR  Sense 5' L Vl3

<400> SEQUENCE: 43
gctctgtgac ctcctatgag ctg                                           23

<210> SEQ ID NO 44
<211> LENGTH: 30
<212> TYPE: DNA
<213> ORGANISM: Artificial Sequence
<220> FEATURE:
<223> OTHER INFORMATION: Synthetic construct -continued

```
<220> FEATURE:
<221> NAME/KEY: misc_feature
<223> OTHER INFORMATION: oePCR Primers JH1

<400> SEQUENCE: 44
ggaggcgctc gagacggtga ccagggtgcc                               30

<210> SEQ ID NO 45
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: oePCR Primers JH3

<400> SEQUENCE: 45
ggaggcgctc gagacggtga ccagggttcc                               30

<210> SEQ ID NO 46
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: oePCR Primers JH2

<400> SEQUENCE: 46
ggaggcgctc gagacggtga ccattgtccc                               30

<210> SEQ ID NO 47
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: oePCR Primers JH4

<400> SEQUENCE: 47
ggaggcgctc gagacggtga ccgtggtccc                               30

<210> SEQ ID NO 48
<211> LENGTH: 45
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: oePCR Primers VK2

<400> SEQUENCE: 48
ggcgcgccat gggaatagct agccgatgtt gtgatgactc agtct            45

<210> SEQ ID NO 49
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH First PCR Antisense 3' C CH1
```

<400> SEQUENCE: 49
gggaattctc agaggagacg a				21

<210> SEQ ID NO 50
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl First PCR  Sense 5' L Vl7

<400> SEQUENCE: 50
ggtccaattc ycaggctgtg gtg				23

<210> SEQ ID NO 51
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl First PCR  Sense 5' L Vl2

<400> SEQUENCE: 51
ggtcctgggc ccagtctgcc ctg				23

<210> SEQ ID NO 52
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl First PCR  Sense 5' L Vl1

<400> SEQUENCE: 52
ggtcctgggc ccagtctgtg ctg				23

<210> SEQ ID NO 53
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl First PCR  Sense 5' L Vl4/5

<400> SEQUENCE: 53
ggtctctctc scagcytgtg ctg				23

<210> SEQ ID NO 54
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  Second PCR  Antisense Ck 494

<400> SEQUENCE: 54
gtgctgtcct tgctgtcctg ctc				23

```
<210> SEQ ID NO 55
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igl First PCR  Sense 5' L Vl6

<400> SEQUENCE: 55
gttcttgggc caattttatg ctg                                            23

<210> SEQ ID NO 56
<211> LENGTH: 23
<212> TYPE: DNA
<213> ORGANISM: Artificial Sequence
<220> FEATURE:
<223> OTHER INFORMATION: Reverse primer Ig-variable heavy chain 3'CHg1
      adaptor

<400> SEQUENCE: 56
gttgtccacc ttggtgttgc tgg                                            23

<210> SEQ ID NO 57
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  First PCR Antisense 3' Ck 543

<400> SEQUENCE: 57
gtttctcgta gtctgctttg ctca                                           24

<210> SEQ ID NO 58
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: Peptide antigens used for ELISA (AB2-antigen
      protein sequence)

<400> SEQUENCE: 58

Ser Thr Gly Asp Ala Asp Gly Pro Gly Gly Pro Gly Ile Pro Asp Gly
1               5                   10                  15

Pro Gly Gly Asn
            20

<210> SEQ ID NO 59
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: control peptide sequence

<400> SEQUENCE: 59

Leu Pro Thr Thr Met Asn Tyr Pro Leu Trp Ser Gln Ser Tyr Glu Asp
1               5                   10                  15
```

Ser Ser Asn Gln
        20

<210> SEQ ID NO 60
<211> LENGTH: 35
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: oePCR Primers VH4

<400> SEQUENCE: 60
tattcccatg gcgcgccsag gtgcagctgg tggag                              35

<210> SEQ ID NO 61
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Ig-variable heavy chain linker primer 3 SalI
      JH:

<400> SEQUENCE: 61
tattcgcact gcgcggcgtc gacgc                                        25

<210> SEQ ID NO 62
<211> LENGTH: 33
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH Second PCR  Antisense 3' SalI JH1/2

<400> SEQUENCE: 62
tgcgaagtcg acgcctgagg agacggtgac cag                               33

<210> SEQ ID NO 63
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH Second PCR  Antisense 3' SalI JH3

<400> SEQUENCE: 63
tgcgaagtcg acgctgaaga gacggtgacc attg                              34

<210> SEQ ID NO 64
<211> LENGTH: 33
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH Second PCR  Antisense 3' SalI JH6

<400> SEQUENCE: 64
tgcgaagtcg acgctgagga gacggtgacc gtg                               33

```
<210> SEQ ID NO 65
<211> LENGTH: 31
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: IgH Second PCR  Antisense 3' SalI JH4/5

<400> SEQUENCE: 65
tgcgaagtcg acgctgagga gacgtgacca g                                    31

<210> SEQ ID NO 66
<211> LENGTH: 32
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  Specific PCR  Sense  5' AgeI Vk 3-11

<400> SEQUENCE: 66
ttgtgctgca accggtgtac attcagaaat tc                                   32

<210> SEQ ID NO 67
<211> LENGTH: 46
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  Specific PCR  Sense  5' AgeI Vk 3-20

<400> SEQUENCE: 67
ttgtgctgca accggtgtac attcagaaat tgtgttgacg cagtct                    46

<210> SEQ ID NO 68
<211> LENGTH: 46
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Igk  Specific PCR  Sense  5' AgeI Vk 1-9

<400> SEQUENCE: 68
ttgtgctgca accggtgtac attcagacat ccagttgacc cagtct                    46
```

METHOD FOR RECOVERING TWO OR MORE GENES, OR GENE PRODUCTS, ENCODING AN IMMUNORECEPTOR

CROSS REFERENCE TO RELATED APPLICATIONS

This application is a continuation of U.S. application Ser. No. 15/118,676, § 371(c) date Aug. 12, 2016; which is a U.S. National Phase of PCT Application No. PCT/EP2015/053135, filed Feb. 13, 2015, the entire disclosures of which are herein incorporated by reference for all purposes.

REFERENCE TO A SEQUENCE LISTING SUBMITTED ELECTRONICALLY VIA EFS-WEB

The content of the electronically submitted sequence listing (Name: 4650_0010002_SeqListing_ST25.txt; Size: 18,737 bytes; and Date of Creation: Nov. 5, 2021) is herein incorporated by reference in its entirety.

The present invention is related to a method for recovering two or more genes, or gene products, encoding for an immunoreceptor.

Genes encoding proteins from libraries or from natural resources can be isolated in order to make them accessible for therapeutic, diagnostic, scientific or commercial purposes. This applies, in particular, to immunoreceptors.

Immunoreceptors encoded by T- and B cells are assembled from families of germline gene segments through a process termed somatic recombination resulting in each individual cell expressing a distinct receptor. These cells may undergo a subsequent somatic mutation process, termed affinity maturation, that further increases the variety of the immunoreceptors.

If such immunoreceptor has two or more genes, or gene products, encoding for it—as it is the case for antibodies and T-cell receptors where both gene products jointly contribute to the receptors capacity to bind antigen—the maintenance of the original pairing of the two or more genes, or gene products, is key to warrant an authentic and proper function of the resulting protein, once the latter is expressed in a suitable expression system.

Such phenomenon is for example crucial in the recovery of the genes encoding for individual immunoglobulins from a subject's antibodyome. Here, the maintenance of the original immunoglobulin heavy- and light chain (IgH+IgL) pairing, as it occurred in naturally occurring B-cells, is important to produce an authentic recombinant copy of the respective antibody, and thus guarantees its functionality. IgH and IgL are the products of 2 distinct genes and are both required to determine the specificity of an antibody. Each B-cell expresses a distinct set of IgH+IgL and thus possesses a unique antibody specificity.

Another example are T-cell receptor-fusion proteins, which have been derived from T-cell receptors, and feature alpha and beta chains ($\alpha$ and $\beta$), and in which the correct pairing thereof is likewise a requirement for functionality.

While recombinant methods to isolate the immunoglobulin genes from human B cells and to generate a large variety of monoclonal antibodies exist, e.g., phage display, these methods lead to a random pairing of the immunoglobulin heavy- and light chains.

Antibody cloning methods that retain the information of the original immunoglobulin heavy- and light chain pairing, as it occurred in B-cells isolated from selected donors as a source of variety have specific advantages. In particular, such authentic antibodies are expected to have undergone in vivo selection processes that result in the absence of those specificities that could be potentially harmful to the host.

In addition, there is evidence that antibodies with cognate IgH- and IgL-pairing, besides expressing the original specificity of the parental B cell, display better stability, better expressability and other favorable physicochemical properties as compared to antibodies formed of random paired IgH and IgL. These favourable properties are important for screening and large scale production.

Historically, the challenge of obtaining monoclonal antibodies, particularly from human B-cells, has been solved by a variety of cellular B-cell cloning technologies, in which the B-cells are stimulated to divide and/or to produce antibody which production is required to identify either single B cells or mixtures of B cells that produce an antibody of interest. Identification of the B cell clone that expresses the antibody of interest can then be performed by cellular cloning e.g. limiting dilution cloning or by combination of the cellular stimulation with a molecular cloning step and subsequent repetition of the screening process using recombinantly expressed antibodies using suitable methods established in the art.

These cellular cloning methods, e.g. the hybridoma technology, are inefficient, with cloning efficiencies often below 1%, and are thus feasible only in situations where antibodies of interest are expressed by highly abundant B-cells (e.g. in infections, upon vaccination). This, however, is a severe limitation because oftentimes antibodies are meant to be made against targets that are not involved in infection or other conditions creating high B-cell abundance. Examples are found in immune-mediated diseases, neurodegenerative diseases or cancer.

Any technology aiming at the molecular cloning of authentic antibody repertoires, e.g., from a B-cell donation, is thus required to work on the single cell level. Until present, this single-B-cell molecular cloning of antibodies has however not been achieved with a throughput high enough to comprise a full antibodyome of 100.000 or more distinct antibody specificities at affordable cost, or in an acceptable timeline.

SUMMARY OF THE PRESENT INVENTION

It is one object of the present invention to facilitate the isolation of two or more genes, or gene products, encoding for an immunoreceptor.

It is one other object of the present invention to provide a method that delivers an immunoreceptor being encoded by two or more genes, or gene products, which protein has advantages when being used for therapeutic, diagnostic, scientific or industrial purposes.

It is one other object of the present invention to provide a method that is likely to yield an immunoreceptor being encoded by two or more genes, or gene products, which protein is not, or at least to a very low degree, biased by properties other than binding to the desired antigen.

It is one other object of the present invention to allow the maintenance of the original pairing present in a single cell, of two or more genes, or gene products, encoding for an immunoreceptor during isolation.

It is one other object of the present invention to allow high throughput screening of a library of cells that have the potential of expressing an immunoreceptor that is encoded by two or more genes, or gene products, or its mRNA.

EMBODIMENTS OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an", and "the" include singular and/or plural referents unless the context clearly dictates otherwise. It is moreover to be understood that, in case parameter ranges are given which are delimited by numeric values, the ranges are deemed to include these limitation values.

According to one aspect of the invention, a method for recovering two or more genes, or gene products, or cDNAs, encoding for an immunoreceptor having two or more subunits, is provided, which two or more genes, or gene products, are comprised in a given source cell. Said method comprises the following steps:
  a) encapsulation of source cells together with an mRNA capturing moiety in microreactors
  b) lysis of the cells in the microreactors, release of the cellular mRNA in the lumen of the microreactors, and subsequent attachment thereof to the mRNA capturing moiety
  c) reverse transcription of the mRNA attached to the mRNA capturing moieties to obtain the corresponding cDNA gene products
  d) creating a construct that encompasses the two or more gene products encoding for the subunits of the immunoreceptor, and
  e) cloning of the PCR product into a plasmid vector to obtain a bi- or multicistronic expression construct.

In such way, a Plasmid library is created which contains the cDNAs encoding for the immunoreceptors of a given source cell population.

As used herein, the term "immunoreceptor" refers to a protein that has two or more subunits and is capable of binding, specifically, to a given target molecule, preferably a protein. Such immunoreceptor is, for example, an antibody, with its heavy and light chains, or a T-cell receptor, with its alpha and beta chains.

As used herein, the term "target molecule" encompasses molecules against which an immunoreceptor is to be made, e.g., for therapeutic, diagnostic, analytic, scientific or industrial purposes. This can encompass peptides, proteins, glycoproteins, carbohydrates, nucleic acids, protein-nucleic acid complexes, and small molecules, in particular receptor proteins, cytokine proteins, protein aggregates (in particular pathological aggregates, like Abeta, Tau or α-synuclein), protein complexes such as MHC-antigenic peptide complexes and structural proteins.

As used herein, the term "specificity for a given target molecule" defines the ability of an immunoreceptor to react with a given target, but not with others. Specificity is dependent on chemical composition, physical forces, and molecular structure at the binding site.

As used herein, the term "source cell" relates to a cell that has the potential of expressing said immunoreceptor, or its mRNA, i.e., to the cell that is the source of the genes encoding for said immunoreceptor. This can relate, e.g., to a cell or a collection of cells isolated from nature, e.g., from a donor. These cells can be, e.g., B-cells from a donor, wherein each of which encodes for another antibody. In like manner, the source cells can be T-cells from a donor, wherein each of which encodes for another T-cell receptor.

Hence, the two or more genes, or gene products, or cDNAs, encoding for said antibody, or T-cell receptor, are meant to be recovered for further use thereof.

As used herein, the term "microreactors" refers to physical entities which allow a three-dimensional encapsulation of the source cells. In a preferred embodiment, these microreactors have a spheroidal shape, float freely and can be handled in micro- or microfluidic environments.

As used herein, the term "reverse transcription of the mRNA" refers, among others, to reverse transcription PCR, also called RT-PCR, where a single stranded mRNA template is transcribed into double stranded DNA, sometimes called cDNA.

It is important to understand that this approach allows the simultaneous recovery of two or more genes, or gene products, encoding for an immunoreceptor having two or more subunits. Thus, the specific combination of the two or more subunits is conserved throughout the entire process that is subject of the present invention. This applies, for example, for immunoglobulin-based antibodies, which consist of a light chain and a heavy chain, which are specific for one another, i.e., the specific pairing of their respective chains is mandatory for a proper function of the respective antibody. The inventors consider this feature as a specific advantage of the invention because other methods from the prior art do not provide the conservation of the specific pairing of heavy and light chain, and can thus result in dysfunctional antibodies.

The source cells can be cells from a collection of cells, e.g., a library of cells and/or a collection of cells isolated from nature, e.g., from a donor. In a preferred embodiment, said collection or library can contain up to 1.000.000 distinct cells (thus encoding up to 1.000.000 distinct antibodies).

The fact that the mRNA encoding for the different subunits of the immunoreceptor is first spatially linked by attachment to a capturing moiety and then physically joined by overlap extension PCR, and/or the fact that the PCR product is cloned into a bi- or multicistronic expression construct that comprises the two or more cDNAs encoding for the different subunits of the immunoreceptor ensures that the two or more genes, or gene products, are processed and recovered in combination, and said specific combination of the two or more subunits is conserved throughout the entire process.

Overlap extension PCR (called herein oePCR) is a variant of PCR. It is used to link smaller DNA fragments into a larger polynucleotide (Embleton et al., 1992).

As in most PCR reactions, two primers—one for each end—are used to amplify a given nucleotide sequence. To link two DNA molecules, special primers are used at the ends that are to be joined. For each molecule, the primer at the end to be joined is constructed such that it has a 5' overhang complementary to the end of the other molecule. Following annealing when replication occurs, the DNA is extended by a new sequence that is complementary to the molecule it is to be joined to. Once the amplification of the two DNA molecules reaches a critical concentration the two distinct genes will pair at the position where the two complimentary primer sequences anneal.

The overlapping complementary sequences introduced will serve as primers for the elongation of the heteroduplex and result in the fusion of the two sequences. Further amplification of the heteroduplex occurs upon annealing of the two primers at the free ends of the newly formed heteroduplex (those that were not part of the linkage process).

An optional additional amplification step is carried out in a second PCR using nested primers specific for the free ends of the two separate genes.

This method has an advantage over other gene linking techniques in not requiring restriction endonucleases (or ligases). Thus, oePCR enables the confirmation/transformation of the mere "spatial linkage" of two separate genes on the mRNA capturing matrix beads into a covalent linkage in the form of a heteroduplex DNA molecule.

Preferably, after step c) an additional quality control step may be carried out, in which the uniformity of the mRNA attachment to the mRNA capturing moieties is assessed. According to a particularly preferred embodiment, the mRNA capturing moieties being devoid of attached mRNA and those that form aggregates of two or more moieties are eliminated in this step.

According to a preferred benchmark, ≥30% of the mRNA capturing moieties have an mRNA attached. More preferably, ≥40%, ≥50%, ≥60%, ≥70%, ≥80% or, most preferably, ≥90% of the mRNA capturing moieties have an mRNA attached.

Preferably, after step d) an additional quality control step may be carried out, in which the uniformity of the distribution of the two or more genes, or gene products, encoding for the different subunits is assessed. According to a preferred benchmark, ≥30% of the mRNA capturing moieties contain a clonable amplification product (cDNA). More preferably, ≥40%, ≥50%, ≥60%, ≥70%, ≥80% or, most preferably, ≥90% of the mRNA capturing moieties contain a clonable amplification product Preferably, after step d) an additional quality control step may be carried out, in which a cross-contamination rate is assessed, e.g., by determining the diversity of the paired IgH- and IgL genes by sequence analysis of a representative sample of the joined subunits, or genes, respectively. According to a preferred benchmark, the latter is ≤35%. More preferably, the cross-contamination rate is ≤30%, ≤25%, ≤20%, ≤15%, ≤10% or, most preferably, ≤5% of the mRNA capturing moieties containing a clonable amplification product.

In step c), the selection of nucleic acid molecules used to capture the mRNA and to prime reverse transcription can for example be dominated by mRNA capturing moieties. In some embodiments, the latter may display specific capturing nucleic acid sequences attached which are complementary to all mRNA of a given cell such as oligo dT or random hexamer primers.

In other embodiments, the nucleic acid molecules used for mRNA capturing an priming of reverse transcription can be designed in such way that only specific mRNAs are transcribed, e.g., mRNAs encoding for the HC and LC chains of an immunoglobulin.

According to a preferred embodiment, the method of the invention further comprises, after step c), the step of amplifying the construct encompassing the two or more gene products encoding for the subunits of the immunoreceptor.

To do so, specific PCR primers are being used. In order, for example, to amplify the construct encoding for an antibody, primers can be used which are specific to the variable region ("v-region") of the rearranged (V(D)J rearrangement) immunoglobulin heavy- and light chain cDNA after V(D)J recombination (assuming that the light chain cDNA gene product follows downstream). Specific PCR primers suitable for this purpose are for example described in Wardemann, et al. (2003).

Likewise preferably, after step c), a further quality control step may be carried out which comprises the steps of
 (i) monitoring cDNA synthesis on the mRNA capturing moieties, and
 (ii) exclusion of aggregated mRNA capturing moieties.

This approach helps to eliminate cross talk between two or more mRNA capturing moieties from different microreactors, which can lead to a disruption of the HC/LC pairing.

The monitoring of the cDNA synthesis on the mRNA capturing moieties can for example be carried out with methods similar to those used in reverse transcription RT-PCR, where the progress of the RT-PCR is monitored, e.g., by means of DNA probes that bind to the matrix, which probes have a fluorescent reporter at one end and a quencher at the opposite end.

According to another preferred embodiment of the invention, the creation of a construct that encompasses the two or more gene products encoding for the subunits of the immunoreceptor, as set forth in step d), is accomplished by amplifying the cDNA by overlap extension PCR.

According to another preferred embodiment of the invention, the step of amplifying the construct encompasses the use of a nested PCR (also called nPCR herein).

This approach may not only provide an amplified PCR product, so that enough cDNA copies are available for cloning, as set forth in step e) above. It further allows the introduction of suitable restriction sites and provides sufficient specificity to only amplify the two or more gene products encoding for the subunits of the immunoreceptor.

Nested PCR is a modification of polymerase chain reaction intended to reduce non-specific binding in products due to the amplification of unexpected primer binding sites. Polymerase chain reaction itself is the process used to amplify DNA samples, via a temperature-mediated DNA polymerase. The products can be used for sequencing or analysis, and this process is a key part of many genetics research laboratories, along with uses in DNA fingerprinting for forensics and other human genetic cases. Conventional PCR requires primers complementary to the termini of the target DNA. A commonly occurring problem is primers binding to incorrect regions of the DNA, giving unexpected products. Nested polymerase chain reaction involves two sets of primers, used in two successive runs of polymerase chain reaction, the second set intended to amplify a secondary target within the first run product.

According to another preferred embodiment of the invention, the method further comprises the step of inserting regulatory elements into the PCR product that support expression of the cDNAs. Such regulatory elements are, for example, cleavage sites, signal peptides or promoters.

According to another preferred embodiment of the invention, the microreactors are lysed, or disrupted, after step b), step c) or step d).

In case the microreactors consist of alginate (as discussed elsewhere herein), lysis may be accomplished by merely adding EDTA (Ethylendiamintetraacetate) to reduce the titer of bivalent cations (e.g., $Ca^{2+}$) in the medium, which the alginate needs to maintain its gel-like status. Alternatively, alginase enzymes can be used, which digest alginates.

Alginases are poly(beta-D-mannuronate) lyases that catalyze the cleavage of polysaccharides containing beta-D-mannuronate residues, to provide oligosaccharides with 4-deoxy-alpha-L-erythro-hex-4-enopyranuronosyl groups at their ends. Alginases belong to the family of lyases, their systematic name is poly(beta-D-1,4-mannuronide) lyase. Other names in common use include alginate lyase I, alginate lyase, alginase I, and alginase II.

Because the mRNA capturing moieties are capable of capturing the entire mRNA of a given source cell, the decisive step to ensure the cell-specific pairing of the two or more genes, or gene products, or cDNAs, encoding for the subunits of the immunoreceptor of interest, is accomplished as soon as the entire cellular mRNA is bound to the mRNA capturing moieties. As set forth elsewhere herein, this specific pairing is mandatory for a proper function of the respective immunoreceptor of interest.

This being said, the earliest possible moment to lyse the microreactors (without losing the specific pairing of the two or more genes, or gene products, or cDNAs, encoding for the subunits of the immunoreceptor of interest), is after step b), because then the entire cellular mRNA (including the mRNAs encoding for the subunits of the immunoreceptor of interest) is captured on a given mRNA capturing moiety.

Preferably, between ≥1 and ≤100 mRNA capturing moieties are being used per microreactor. More preferably, between ≥5 and ≤50 mRNA capturing moieties are being used per microreactor.

In some embodiments, the later steps, i.e., (i) the reverse transcription of the mRNA attached to the mRNA capturing moieties to obtain the corresponding cDNA (step c), (ii) the creation of a construct that encompasses the two or more gene products encoding for the subunits of the immunoreceptor (step d), and/or (iii) the cloning of the PCR product into a plasmid vector to obtain a bi- or multicistronic expression construct (step e) can take place in solution, i.e., outside the microreactor, without bearing the danger that the specific pairing of the two or more genes, or gene products, or cDNAs, encoding for the subunits of the immunoreceptor of interest will get lost.

However, according to other embodiments some or all of these steps still take place within the microreactors.

According to another preferred embodiment of the invention, the mRNA capturing moieties are emulsified with suitable primers and at least one polymerase after step b).

For this purpose, the mRNA annealed to the mRNA capturing moieties (e.g., the poly(dT) magnetic beads), is preferably collected, washed and emulsified with primers, reverse transcriptase and thermostable DNA polymerase to carry the out RT-PCR, optionally followed by oePCR.

Such process can be accomplished, e.g., by pelleting the poly(dT) magnetic beads having captured the cellular mRNA on a magnetic rack, following washing and resuspension steps. The beads can then be suspended in a suitable RT-PCR mixture, and the resulting suspension is added to a stirring vessel containing an oil phase. The resulting emulsion is then added to suitable PCR plates or tubes and placed in a thermocycler.

According to another preferred embodiment of the invention, the immunoreceptor is an antibody having at least two subunits, or a T-cell receptor having at least two subunits. While in an antibody, the subunits are the heavy and light chains, in a T-cell receptor-like antibody the subunits are the alpha and beta chains.

As used herein, the term "antibody" shall refer to an immunoreceptor that essentially relies on the immunoglobulin concept. When isolated from a source cell, i.e., a cell that has the potential of expressing said immunoreceptor, said antibody is still in the conventional Ig format (IgG, IgD, IgE, IgA and/or IgM). Preferably, this will as well be the format which is subject of the screening process described elsewhere herein, in which process a library of expressor cells is screened for one cell that expresses an immunoreceptor that has specificity for a given target molecule.

This however does not mean that the immunoreceptor which is then used for therapeutic, diagnostic, analytic, scientific or industrial purposes is still in that format. It may well be present as a fragment or derivative thereof, e.g., as an scFv, Fab and/or F(ab). Likewise, the immunoreceptor which is then used for therapeutic, diagnostic, analytic, scientific or industrial purposes can be a new antibody format, for example a bi- or trispecific antibody construct, Diabody, Camelid Antibody, Domain Antibody, bivalent homodimer with two chains consisting of scFvs, IgA (two IgG structures joined by a J chain and a secretory component), shark antibody, antibody consisting of new world primate framework plus non-new world primate CDR, dimerised construct comprising CH3+VL+VH, and antibody conjugate (e.g., antibody or fragments or derivatives linked to a toxin, a cytokine, a radioisotope or a label). This list is however not restrictive.

The skilled person knows how to translate a given antibody which is still in the conventional Ig format, and which has proved to have specificity for a given target, into a fragment or derivative thereof as set forth above, or into a new antibody format as set forth above.

Another preferred format is a "reverse chimera format", in which the human variable region is isolated from a human antibody obtained with the present method, and fused to a non-human constant region, e.g., a murine constant region. This reverse chimera format provides particular advantages for selected diagnostic, analytic, scientific or industrial applications, where a complete infrastructure relying on nun-human antibodies, in particular murine or rabbit antibodies, has been established, including assays formats, histology formats and screening formats, and where for example labelled anti-mouse antibodies are used to label a target-specific detection antibody (which is murine and has thus a murine Fc region). In such environment, a fully human detection antibody would not be compatible with the remaining environment.

A reverse chimera format made from a human variable region obtained with the present method thus combines the advantages of the present invention (superior binding quality due to conserved heavy- and light chain pairing) with the compatibility of the produced antibody with standard assay formats, histology formats or screening formats.

Such reverse chimera can be generated in like manner as chimeric antibodies, e.g., by established recombinant methods, as for example discussed in Boulianne et al. (1984) or Morrisson et al. (1984).

T-cell receptors (TCR) are molecules found on the surface of T lymphocytes. T-cell receptors are responsible for recognizing antigens bound to the major histocompatibility complex (MHC) molecules. T-cell receptors are usually composed of two different protein chains, namely an alpha (α) and beta (β) chain (in 5% of T lymphocytes, the T-cell receptor consists of gamma and delta (γ/δ) chains).

When the TCR engages with antigenic target and the MHC, the T lymphocyte is activated through a series of biochemical events mediated by associated enzymes, co-receptors, specialized adaptor molecules, and activated or released transcription factors.

Recombinant T-cell receptor fusion proteins have recently emerged as a means to target peptide antigens which are presented as a complex of peptide and major histocompatibility complex (MHC) on the cell surface-.

For this purpose, soluble variants of T-cell receptors can be created, e.g., by fusing a TCR to an immune-stimulator. These fusion proteins can be used to target originally intracellular antigens. Such intracellular antigens are not accessible by other targeted therapies, in particular, not by antibodies. Through this approach, various cancers can be targeted by using soluble variants of T-cell receptors directed against cancer specific antigens (Card et al., 2004).

According to another preferred embodiment of the invention, the immunoreceptor is a therapeutic protein (e.g., a protein that is used in a human or animal patient to treat a disease, or avoid its occurrence), a protein for diagnostic or scientific purposes (e.g., a protein that is used to detect an analyte), or a protein for commercial purposes (e.g., a protein that is used in an industrial process, e.g., for the isolation or purification of a given compound).

According to another aspect of the invention, a method of creating a library of expressor cells is provided, in which library each cell is capable of expressing two or more genes, or gene products, encoding for the subunits of the immunoreceptor recovered according to the method of claim 1, which method comprises the following steps:
  g) Transfecting expressor cells with the bi- or multicistronic expression construct, and
  h) encapsulating the expressor cells into microreactors As elsewhere discussed, these microreactors can, in principle, be similar to those used for the source cells, i.e., the cells that have the potential of expressing the immunoreceptor of interest, or its mRNA. However, these microreactors can also be bigger, because, in a preferred embodiment, the expressor cells are expanded after encapsulation.

Preferably, these expressor cells are cells commonly used for the heterologous expression of therapeutic, diagnostic, analytic, scientific or industrial proteins. The term "expressor cells" thus encompasses bacterial cells (like *E. coli*), fungal cells (like *Pichia, Aspergillus, Saccharomyces, Schizosaccharomyces, Hansenula, Arxula*, or *Trichoderma*), mammalian cells (like CHO, COS, HEK, HeLa, 3T3, NSO or HepG2, PER.C6), or insect-cells.

It is important, in this context, that the terms "source cell" and "expressor cell" mean two different things. The term source cell relates to the cell that is the source of the genes encoding for a given protein, e.g., a cell or a collection of cells isolated from nature, e.g., from a donor.

In contrast thereto, the term "expressor cell" shall refer to a cell that is actually used in the method according to the invention for expressing said immunoreceptor, to obtain it in large quantities and purify it for further use.

Preferably, it is assured in step g) that each expressor cells is transfected with one bi- or multicistronic expression construct only. This can be accomplished, preferably, by limiting dilution processes well known to the skilled person.

Likewise preferably, it is assured in step h) that only one expressor cell is encapsulated per each microreactor. This can be accomplished, preferably, by titrating the number of viral particles per cell so that <<100% are transduced e.g. 10% of cell or 30% of cells (limiting dilution).

Preferably, it is provided that the encapsulated expressor cells are cultured under conditions which allow protein expression and/or proliferation of the cells.

In a preferred embodiment, it is provided that, prior to the encapsulation in step h), the transfected cells are incubated under conditions that allow protein expression. This embodiment allows to sort out those cells which are dysfunctional or do not express the transgene, e.g., the immunoreceptor combined with a marker gene (fluorescent marker/surface marker).

Preferably, after step g) or h) an additional quality control step may be carried out, in which it is checked whether or not the infected cells are capable of expressing a functional antibody.

According to another aspect of the invention, a method of screening a library of expressor cells as created according to the above method is provided, which method is meant to detect one cell (or, respectively, its clonal progeny in the microreactor) that expresses an immunoreceptor that has specificity for a given target molecule, which method comprises at least one of the following steps:
  i) use of a labeled target that is capable of entering into the microreactors and bind to an immunoreceptor expressed by the expressor cell comprised therein, and/or
  j) detecting immunoreceptor expressed by the expressor cell that has escaped from the microreactors and is now in the supernatant in combination with serial fractionation of the microreactor culture As regards the latter option, established screening technology capable of detecting immunoreceptors in the meaning of the present invention can be used.

As regards the former, the concentration of immunoreceptor inside the microreactors reaches peak levels faster than that in the supernatant fluid. This temporal retention of immunoreceptors can be exploited for screening using a washing step to dilute the immunoreceptor concentration in the supernatant fluid surrounding the microreactors prior to intra-microreactor-detection of antibody specificity. Microreactors that stain positive for a fluorescently labelled antigen are then sorted and either left intact for, e.g., an additional confirmatory screening or disrupted to allow further growth of the antigen-reactive/specific cell clone and the production of monoclonal antibody.

As regards the latter, the supernatant fluid surrounding the microreactors obtained after sedimentation or centrifugation of the microreactor culture can be directly tested for the presence of immunoreceptors with the desired function or other property.

In each case, the respective experiment will provide a positive result ("hit") if the immunoreceptor expressed by the respective expressor cell has specificity for the labelled target.

Such label for labelling the target may consist, e.g., of a radioisotope, an enzyme, a luminescent entity, a fluorescent entity, a phosphorescent entity, a metal-containing particle (e.g., a gold-containing particle), an X-ray dense entity, an antibody or the like. Finding a suitable label is entirely within the routine of the skilled artisan.

It is to be understood that the present invention involves three individual methods, or substeps, which are linked to one another by the same inventive concept, namely (i) a method for recovering two or more genes, or gene products, or cDNAs, encoding for an immunoreceptor, (ii) a method of creating a library of expressor cells on the basis of the recovered genes, or gene products, or cDNAs, and (iii) a method of screening such library of expressor cells.

Each of these three methods has a right on its own. However, it is of course contemplated that the method of the invention can comprise, in a preferred embodiment substeps (i) and (ii), (ii) and (iii), or (i)-(iii).

According to another preferred embodiment of the invention, the mRNA capturing moieties are beads or particles, preferably magnetic beads or particles. Preferably, the mRNA capturing moieties comprise oligo dT DNA sequences bound to their surface.

In this context, magnetic beads comprising oligo dT DNA sequences are preferred. One example for such type of beads are Dynabeads® Oligo (dT)25 provided by Life Technologies. The use of oligo dT beads relies on base pairing between the poly A tail of messenger RNA and the oligo dT sequences bound to the surface of the beads. oligo dT beads can thus be used to recover the entire mRNA of a given cell. After annealing, the vial is placed on a magnet to concentrate the beads with their bound mRNA at the side of the tube. The supernatant containing unwanted contaminants is discarded. The protocol can be performed in 15 minutes, without the need to prepare total RNA or perform any other purification steps. The oligo dT bound to the bead surface can be used to both capture the mRNA and act as a primer for reverse transcriptase during first strand cDNA synthesis.

According to another preferred embodiment of the invention, the bi- or multicistronic expression vector is a 2A peptide-linked multicistronic vector with or without combination with an IRES (internal ribosome entry site) sequence.

2A peptide-linked multicistronic vectors are for example described in Szymczak et al. (2004). However, the skilled person will readily understand that other suitable bi- or multicistronic expressions are also encompassed by the scope of the present invention, and can be used in its context without the need for additional inventive steps.

Materials and technologies for preparing microreactors in the meaning of the present invention are well known to those trained in the art. In principle, all technologies can be used that a) produce appropriately sized capsules, and that b) produce capsules with high monodispersity.

Furthermore, in preferred embodiments materials may be used that a) result in capsules with the desired permeability for all or some reactants used in their presence, and that b) result in capsules that are stable for all reaction conditions employed in their presence, and that c) show low or no inhibitory effects for the enzymatic reactions performed within the capsule structure. It is self-evident that the cell(s) and/or transformed and/or amplified nucleic acid(s) should not be able to leave the capsule until lysis of the capsule.

For practicing the method of the present invention, it may be necessary to employ capsule materials that show low or no inhibitory effects for the enzymatic reactions such as amplification or sequencing reactions performed within the capsule structure. Capsule materials with appropriate low inhibitory effects on amplification and sequencing reactions are those listed above. Many capsule materials allow enclosed cells to proliferate. It is furthermore desirable to employ a capsule material that is stable against all reaction conditions employed. Preferably, the capsules are not disintegrated by chemical, physical and mechanical stress induced by, for instance, growth of cells, cell lysis, in vitro amplification, or DNA sequencing. Preferred capsule materials are those discussed herein elsewhere.

More preferably, the microreactors for practising the present invention are produced by a method for the production of single droplets as described by Serp et al. (2000). Other technologies providing suitable results are the flow focusing technology (Cellena®, Ingeniatrics Tecnologías, S.L., Sevilla, Spain), Gomez-Herreros et al (2012), flow focusing nozzles incorporated in microfluidic devices as described in Martinez et al (2012), emulsion polymerization methods (One Cell Systems, Inc., USA) and the Jet-cutter technology as described in Prüße et al. (1998).

Preferably, capsules for use in the invention have a pore size allowing its penetration by part or all of the reactants employed. For practising the method of the present invention, it is advantageous to employ a capsule material that is permeable to a number of reactants that are needed for, e.g. cell propagation, removal of catabolites, amplification, labeling and/or sequencing and that assist purification.

According to another preferred embodiment of the invention, each microreactor comprises one source cell, e. g. one B-cell or one T-cell. The number of cells per microreactor is also known as "degree of occupation" (DOO). In this embodiment, a single cell RT-PCR is actually carried out to recover the mRNA. The specific advantage of this embodiment is that this is one approach which allows the simultaneous recovery of two or more genes, or gene products, encoding for the subunits of the protein having two or more subunits from one cell, as described above.

However, a single cell RT-PCR has so far not been used to recover two or more genes, or gene products, encoding for the subunits of the protein from one cell that is part of a collection of cells, like a library, or a B-cell donation from a human donor, and create a library of expressor cells on the basis thereof, because it was not possible to combine single cell RT-PCR with high throughput methods.

For this reason, single cell RT-PCR was considered to constitute a bottleneck for the recovery of two or more genes, or gene products, encoding for the subunits of the protein having two or more subunits.

This preferred embodiment according to which each microreactor comprises one source cell does, however, not apply to the microreactors used for encapsulating the expressor cells.

The microreactors used for encapsulating the source cells, or preferably one source cell, can however further comprise so-called feeder cells, i.e., cells which do not have the potential of expressing said immunoreceptor, or its mRNA. When lysed, however, these cells can deliver non-immunoreceptor related mRNA that can be helpful to saturate the mRNA capturing entities.

Preferably, the microreactors comprise a material selected from the group consisting of:
 hydrogel-forming polymers, preferably poly(diallyldimethylammonium chloride), poly(ethyleneimine), polylysine, polyacrylamides and/or acrylic acids
 cellulose derivatives, preferably carboxymethylcellulose and cellulose esters, and/or
 polysaccharides, preferably agaroses, alginates, carrageenans, pectinates, and/or chitosans These types of microreactors will also be nicknamed "nanoliter reactors" (NLR) herein, even though their volume does not necessarily need to be in the nanoliter range, but can be higher or smaller.

In a particularly preferred embodiment, the microreactors comprise alginate hydrogels crosslinked by bi- or trivalent metal cations. Microreactors comprising alginate are readily penetrated by globular structures such as enzymes and antibodies, and short strand DNA (primers). Large, thread-like DNA molecules such as PCR products penetrate at a much lower rate. Thus temporal immobilization of the PCR products obtained from a single cell in the microreactor is achieved. Microreactors comprising alginate can furthermore be processed by high throughput analysis and flow cytometric sorting. More preferably, the alginate capsule material comprises calcium, barium and/or strontium alginate. It was surprisingly found that barium alginate and strontium alginate microcapsules have a significantly reduced inhibitory effect on polymerase enzymes needed for PCR reactions. Hence, barium and strontium alginate will allow for a much better amplification than calcium alginate.

The process of forming alginate beads and encapsulating cells therein includes, for example, the use of a mixture of alginate and the cells to be encapsulated, which is drawn through polymer-tube micronozzles. The bead diameter can arbitrarily be adjusted by the nozzle geometry and spinning frequencies between 5-28 Hz. Beads are issued from the micronozzle through an air gap towards a curing agent (e.g., $CaCl_2$)solution) contained in a standard lab tube.

According to another preferred embodiment, the microreactors are formed as aqueous droplets in a water/oil emulsion. These types of microreactors will also be nicknamed "emulsion droplets" herein.

Such microreactors can, e.g., be created with the QX100™ Droplet Digital™ PCR System provided by Biorad. In said device, samples and droplet generation oil are loaded into an eight-channel droplet generator cartridge. A vacuum is then applied to the droplet well, which draws sample and oil through a flow-focusing nozzle where monodisperse droplets are formed.

The above discussion refers to both (i) the microreactors used for encapsulating the source cells or for recovering the two or more genes or gene products or cDNAs, encoding for an immunoreceptor, as well as (ii) to those used for encapsulating the expressor cells, i.e., in both cases microreactors can either be formed as aqueous droplets in a water/oil emulsion or from hydrogel-forming polymers, cellulose derivatives and/or polysaccharides, like agaroses, alginates, carrageenans, pectinates, and/or chitosans.

In a preferred embodiment, however, it is provided that the microreactors used for (i) are formed as aqueous droplets in a water/oil emulsion, while the microreactors used for (ii) are those from hydrogel-forming polymers, cellulose derivatives and/or polysaccharides, like agaroses, alginates, carrageenans, pectinates, and/or chitosans.

According to another preferred embodiment of the invention, the microreactors have a diameter of between ≥10 μm and ≤1000 μm.

According to yet another preferred embodiment of the invention, the microreactors have a volume of between ≥0.52 pl and ≤523 nl.

More preferably, the microreactors used for (i) have a volume of between ≥0.5 and ≤5 nl, whereas the mictoreactors used for (ii) have a volume of between ≥25 and ≤150 nl.

In a preferred embodiment, however, it is provided that the microreactors used for (i) are formed as aqueous droplets in a water/oil emulsion, while the microreactors used for (ii) are those from hydrogel-forming polymers, cellulose derivatives and/or polysaccharides, like agaroses, alginates, carrageenans, pectinates, and/or chitosans. Preferably, however, the microreactors used for encapsulating the source cells can be smaller than those used for encapsulating the expressor cells.

The following table gives an overview of the different subtypes of microreactors used in the context of the present invention:

|  | Emulsion droplets | NLR reactors |
|---|---|---|
| Composition | Water/oil | hydrogel-forming polymers, cellulose derivatives and/or polysaccharides, like agaroses, alginates, carrageenans, pectinates, and/or chitosans |
| Exemplary Method of formation | (i) QX10 ™ Droplet Digital ™ PCR System (ii) Vortexing of a water-surfactant-oil mixture with glass or steel beads (400 nm diameter) | polymer-tube micronozzles |
| Preferred use | encapsulating the source cells, recovering gene products, or cDNAs, encoding for the immunoreceptor, plus creation of the plasmid library | encapsulating expressor cells, creating library of expressor cells and subsequent protein expression |

-continued

|  | Emulsion droplets | NLR reactors |
|---|---|---|
| Preferred size for this preferred use | Relatively smaller, which is advantageous for the molecular biology process carried out | Relatively bigger, which is advantageous for the cell cultivation and protein expression carried out |
| Preferred size for this preferred use | Relatively smaller, which is advantageous for the molecular biology process carried out | Relatively bigger, which is advantageous for the cell cultivation and protein expression carried out |
| Preferred volume | ≥0.5 and ≤5 nl | ≥25 and ≤150 nl |

Types of Microreactors Disclosed Herein

According to still another preferred embodiment of the invention, the microreactors have a spheroidal shape.

According to another preferred embodiment of the invention, the source cell is from a collection of cells members of which comprise gene products for different immunoreceptors. Preferably, the source cell is a mammalian cell selected from the group consisting of immature or mature B-cells, or T-cells.

In this embodiment, the collection of cells is for example a collection of mature B-cells, e.g., memory B-cells. Such collection may be a collection of cells compiled from B-cell donations from different donors, as well as a collection of all B-cells from a given donor, the fraction thereof, or at least which, as such, comprises the antibodyome, i.e., the complete set of antibodies that are encoded by the entirety of matured B-cells of said donor, or fraction thereof.

Immature or mature B-cells are B-cell types in which the VDJ rearrangement and the VJ rearrangement have already taken place. This means that these cells have already randomly combined variable, joining and diverse gene segments in such way that unique rearranged genes encoding for a unique heavy chain (VDJ) and a unique light chain (VJ) are obtained.

Preferably the B-cells are plasma B-cells or memory B-cells. Plasma B-cells (also known as plasma cells, plasmocytes, and effector B-cells) are large B-cells that have been exposed to antigen and produce and secrete large amounts of antibodies, which assist in the destruction of microbes by binding to them and making them easier targets for phagocytes and activation of the complement system. They are sometimes referred to as antibody factories. An electron micrograph of these cells reveals large amounts of rough endoplasmic reticulum, responsible for synthesizing the antibody, in the cell's cytoplasm. The cells undergo apoptosis when the inciting agent that induced immune response is eliminated. This occurs because of cessation of continuous exposure to various colony-stimulating factors which is required for survival.

Memory B-cells are formed from activated B-cells that are specific to the antigen encountered during the primary immune response. These cells are able to live for a long time, and can respond quickly following a second exposure to the same antigen.

T-cells, or T lymphocytes, are a type of lymphocytes that play a central role in cell-mediated immunity. They can be distinguished from other lymphocytes, such as B cells, by the presence of a T-cell receptor (TCR) on the cell surface. Different types of T-cells exist, namely, Helper, Cytotoxic, Memory, Regulatory and Natural Killer T (NKT)-cells.

Just like B cells, T-cells undergo, during thymocyte development, essentially the same sequence of ordered recombination events as that described for immunoglobulins. D-to-J recombination occurs first in the β chain of the TCR. This process can involve either the joining of the $D_\beta1$ gene segment to one of six $J_\beta1$ segments or the joining of the $D_\beta2$ gene segment to one of seven $J_\beta2$ segments. DJ recombination is followed (as above) with $V_\beta$-to-$D_\beta H_\beta$ rearrangements. All gene segments between the $V_\beta$-$D_\beta$-$J_\beta$ gene segments in the newly formed complex are deleted and the primary transcript is synthesized that incorporates the constant domain gene ($V_\beta$-$D_\beta$-$J_\beta$-$C_\beta$). mRNA transcription splices out any intervening sequence and allows translation of the full length protein for the TCR $C_\beta$ chain. The rearrangement of the alpha (α) chain of the TCR follows β chain rearrangement, and resembles V-to-J rearrangement described for Ig light chains (see above). The assembly of the β- and α-chains results in formation of the αβ-TCR that is expressed on a majority of T-cells.

The specificity of T-cells is MHC-restricted, thus TCRs recognize mainly intracellularly processed linear peptide antigens in the context of MHC molecules. This is in marked contrast to the recognition mode of B-cells, which via soluble or membrane antibodies recognize three-dimensional target structures of their cognate antigen without any involvement of MHC molecules, without the requirement of this being complexed to the MHC. Thus, T and B-cells represent two fundamentally different recognition modes of the specific immune system. Antibodies displaying a MHC-restricted mode of antigen recognition (TCR-like antibodies) seem not to occur naturally but can be induced by hyperimmunisation of laboratory animals. However, it has been difficult to generate such specificities to a broad variety of peptide-MHC complexes and with the required specificity and affinity.

According to another preferred embodiment of the invention, the source cells are taken from one or more donors. Preferably, such donor is a human donor. Likewise, such donor can be from rabbit, mouse, pig, rat, cow and non-human primates.

More preferably, such donor is a donor that has shown reduced or attenuated symptoms with respect to a given disease, has demonstrated retarded disease progression, or has turned out resistant with respect to said disease. Such donor may have an increased likelihood to comprise a source cell, e.g., a B memory cell, that encodes for a therapeutic protein, e.g., an antibody, that may have therapeutic, protective or retarding effect with respect to said disease, e.g., because it is an antagonist to a cancer-mediating cytokine, because it binds to a given pathogen, or because it binds to a receptor involved in an immune response.

According to another preferred embodiment of the invention, the two or more genes, or gene products, encoding for the subunits of the protein are the Immunoglobulin (Ig) heavy chain gene (VDJ rearranged) and the Immunoglobulin (Ig) light chain gene (VJ rearranged). These genes are also termed $V_H$ and $V_L$, or κ and λ genes.

Alternatively, the two or more genes, or gene products, encoding for the subunits of the protein are the TCR alpha chain gene (rearranged) and the TCR beta chain gene (rearranged).

According to another preferred embodiment of the invention, the method further comprises the step of inserting cDNA encoding for Ig constant H and/or Ig constant L subdomains into the PCR product.

Alternatively the method further comprises the step of inserting cDNA encoding for TCR alpha and TCR beta chain into the PCR product.

Furthermore, it is preferred that the immunoreceptor issued for the treatment or diagnosis of a disease. Said disease is, preferably, a human or animal disease, more preferably a neoplastic disease, neurodegenerative disease, infectious disease, immune-mediated disease and/or cardiovascular disease.

Neoplastic diseases encompass malignant diseases like tumors, cancers and the like. Immune-mediated diseases encompass autoimmune diseases. Neurodegenerative diseases encompass diseases that affect the integrity of the central and/or the peripheral nervous system. Infectious diseases encompass diseases caused by parasites, protozoans, prokaryotes, viruses, prions, and fungi. Immune-mediated diseases encompass diseases that are characterized by a dysfunction of the immune system, e.g., because the immune system is overactive or underactive. Cardiovascular diseases encompass any disease that affects the cardiovascular system, principally cardiac disease, vascular diseases of the brain and kidney, and peripheral arterial disease.

BRIEF DESCRIPTION OF THE EXAMPLES AND DRAWINGS

Additional details, features, characteristics and advantages of the object of the invention are disclosed in the subclaims, and the following description of the respective figures and examples, which, in an exemplary fashion, show preferred embodiments of the present invention. However, these drawings should by no means be understood as to limit the scope of the invention.

EXPERIMENTS

Recombinant Display of a Complete Antibody Repertoire (Antibodyome) from a Human Subject or from an Animal Species.

Human memory B-cells are used as starting material for the recombinant display of a human antibodyome. The memory B-cell pool of a subject preserves the antibody specificities and possibly also antibody frequencies generated during previous antigen encounters (McHeyzer-Williams and Ahmed (1999), Bernasconi et al. (2002).

Alternatively, all types of B-cells such as Plasma Cells, Pre-Plasma Cells, B1 B-cells and immature B-cells or hybridoma cells of human or non-human origin can be processed by this technology.

1. Capturing of Antibodyome mRNA by Means of NLR 1.1 Human Memory B-Cells

Memory B-cells are isolated from peripheral blood monocytic cells by cell sorting (MoFlo XDP cell sorter, Beckman-Coulter, Nyon, Switzerland) using as sort criteria, the expression of the pan B-cell marker CD22, combined with the absence of expression of surface IgM, IgD as markers of immature B-cells. Other combinations of surface markers such as CD19, CD27 in- or without combination with surface expressed IgG could also be used.

1.2 Co-Encapsulation of memoryB-Cells and mRNA Capturing Matrix Beads in Nanoliter Reactors 100,000 CD22-positive, IgM-, IgD-, IgA-negative B-cells are then used for encapsulation in NLR together with mRNA capturing Dyna beads. 20,000 surrogate B cells expressing human IgG are used for emulsification in emulsion droplets together with mRNA capturing Dynabeads using the QX100 droplet generator.

1.2.1 Co-Encapsulation of Antibody Producing Cells and mRNA Capturing Matrix Beads in Nanoliter Reactors Antibody producing cells were encapsulated at a degree of occupation (DOO) of 1 together with 5 oligo dT-doted Dynabeads (1 B-cell and 5-50 Dynabeads per NLR).

20,000 antibody producing cells" were resuspended in 1.6 ml encapsulation buffer and $0.5-5 \times 10^6$ mRNA capture matrix beads (Dynabeads) were added. 6.4 ml sterile-filtered 2.5% alginate solution (Pronova) was added and mixed gently. The alginate-cell-magnetic bead suspension was processed with a laminar jet break-up encapsulator through a 150 μm diameter nozzle at 700 Hz.

Droplets were collected in a continuously stirred beaker filled with 100 ml hardening solution. The alginate carriers were allowed to stabilize for 15 min to form NLRs. The NLRs were recovered from the hardening solution by sieving and were washed twice in 80 ml encapsulation buffer. NLRs were collected in encapsulation buffer at 4° C./RT and subjected to large particle sorting to eliminate NLR without a cell and those containing more than 1 cell.

1.3 Lysis of Cells and Capturing of mRNA on Dynabeads Inside NLR

The NLR suspension was allowed to settle for 5 min and supernatant was aspirated. The obtained NLRs were re-suspended gently in equal volume of freshly prepared lysis buffer and were incubated at RT, 20 RPM for 30 min to allow for complete cell lysis.

1.4 Dissolution of NLR, Washing and Retention of mRNA Capturing Matrix

The lysis reaction was filtered, retaining the NLR which were washed trice with encapsulation buffer. The washed NLR were dissolved by treatment with EDTA solution and oligo dT beads were harvested using a magnetic device furnished by the kit manufacturer.

Typically 5-30% of the Dynabeads contain mRNA on their surface.

2. Capturing of Antibodyome mRNA by Means of Emulsion Droplets

In another preferred embodiment of the invention, a water-in-oil emulsion is used to generate microreactors. A water in oil emulsion is formed by mixing a water phase with an oil phase in the presence of suitable surfactants.

The oil phase may consist of mineral oil, silicon oil, Tegosoft DEC, an engineered fluid like Novec 7500, FC-40, FC-43, FC-70, or other common fluorinated oil or any mixture thereof. As surfactant a detergent like Triton X-100, Nonidet P-40 (NP-40), Tween 80, Tween 40, Tween 20, ABIL EM 90, ABIL WE 09, sodium dodecyl sulfate or lithium dodecyl sulfate may be used or a fluorinated detergent like Krytox or other perflouropolyether (PFPE) based surfactants or any mixture thereof.

As microreactor stabilizers and PCR reaction enhancers several additives may be added to the water phase of the water in oil emulsion like 2-pyrrolidone, polyvinylpyrrolidone, betaine, DMSO, PEG8000, Pluronic F-68, glycerol, BSA and/or gelatin.

Water in oil emulsions can be produced in several ways. In one embodiment, (i) droplets might be formed by vortexing a water-surfactant-oil mixture with or without the addition of one or several glass or steel beads. The diameter of a bead is 5 mm, 1 mm or, preferably, 400 nm in average. The mixing frequency can be controlled by the usage of a TissueLyser mixer mill instead of a vortex, the setting of choice might be 15-17 Hz.

In another embodiment (ii), water in oil emulsions may be produced by the use of a microfluidic droplet generator as provided by Bio-Rad (QX100™ Droplet Digital™ PCR) or Raindance (RainDrop® Digital PCR). Here, microfluidic chips are used to generate water in oil microreactors of uniform sizes of 1 nl and 1 pl, respectively.

In case of water in oil emulsion droplets, recovery of mRNA capturing moieties, cDNA or PCR products from the microreactors may be achieved by the addition of organic solvents. This organic solvent may be ethanol, 1-propanol, isopropanol, butanol, hexanol, chloroform, acetonitrile, any mixture thereof and/or mixture with water. The process is described in Diehl et al (2006).

2.1. Cell Encapsulation, Cell Lysis, mRNA Capture and Reverse Transcription

Antibody expressing cells were harvested and diluted to $2 \times 10^6$ cells per ml in cell lysis buffer (50 mM Tris-HCl pH 8.3, 50 mM KCl, 50 mM LiCl, 5 mM EDTA, 10 mM DTT). Oligo-dT Dynabeads (Life Technologies, cat no. 61006) were washed once in cell lysis buffer, beads were collected on a dynal magnet (Life Technologies, cat no. 12321D) and supernatant was discarded. Cells were added to the magnetic beads and mixed carefully, the final amounts of cells and beads per 20 μl being 15,000 cells and 180,000 beads. The mixture was kept on ice and transferred to the QX100 droplet generator (Bio-Rad). Directly before emulsion formation in the DG8™ cartridge (Bio-Rad) was started, Proteinase K (Applichem, cat no. A4392) was added to the cells/dynabeads mixture to a final concentration of 0.2 mg/ml. Droplets were generated for eight samples à 20 μl in parallel according to the manufacturer's instructions. As emulsion oil, Pico-Surf™ 2 (2% in Novec 7500) (Dolomite Microfluidics, cat no. 3200281) was used. Eight times 40 μl of emulsions were transferred by pipetting from the cartridge to two separate 1.5 ml reaction tubes (resulting in 2 samples à 160 μl emulsion). Encapsulated cells (see FIG. 6) were lysed by incubation at 70° C. for 15 minutes in a heat block. Thereafter, samples were placed at room temperature and allowed to cool down slowly. This 15 minutes room temperature incubation step facilitated the binding of the cell released mRNA to the oligo-dT dynabeads. In the next step, oligo-dT beads with attached mRNA were recovered by breaking the oil phase by the addition of 1 ml isopropanol to the emulsion and vortexing. The clear solution was placed on top of a spin filter (Thermo Scientific, cat no. F2517-5) and centrifuged for 30 seconds at 3500 rcf. The flow-through was discarded and the collected beads were washed once in 70% ethanol. The oligo-dT dynabeads were resuspended in 300 μl buffer B of the mRNA purification kit (Life Technologies, cat no. 61006) and transferred to a fresh 1.5 ml reaction tube. The beads were collected on the magnet and buffer was replaced by 100 μl of 1× DNase buffer. 2 μl of RNase free DNase I were added subsequently (NEB, cat no. M0303S) and the mix was incubated for 10 min at 37° C. to digest DNA bound to the oligo-dT beads. The reaction was stopped by addition of 1 μl 0.5 M EDTA. The beads were washed twice with 300 μl buffer B of the mRNA purification kit (Life Technologies, cat no. 61006) and once with 300 μl 1× RT buffer of the maxima RT reverse transcriptase (Life Technologies, cat no. EP0742). The supernatant was discarded and the mRNA covered oligo-dT beads were resuspended in a reverse transcriptase mix containing 0.5 mM dNTPs, 1× RT buffer, 20 U RiboLock RNase Inhibitor (Thermo Scientific, cat no. EO0381) and 200 U Maxima Reverse Transcriptase (Life Technologies, cat no. EP0742). The reaction was incubated for one hour at 55° C. Subsequently, the reaction was stopped by raising the temperature to 85° C. for 5 minutes. The oligo-dT beads, with the covalently attached cDNA, were recovered using a magnet.

The supernatant was discarded, beads were resuspended in 20 mM Tris pH 8.0 and stored at 4° C. until further processing.

2.2. Overlap Extension PCR in Emulsion cDNA beads produced as described in example 2.1 were used as template for an overlap extension PCR to link the DNA sequences encoding antibody VH and VL. To ensure the correct linkage of sequences belonging to one antibody and to avoid cross-talk between sequences, this PCR reaction was performed in a single bead emulsion. To this end, beads were diluted in a PCR reaction mix containing 0.25 mM dNTPs, 0.25 µM of each primer (VH4, Vk2, CH, Ck1), 0.25% w/v BSA, 2% w/v Pluronic F-68, 1× buffer A and 1 U KAPA Robust Hotstart Polymerase (Kapa Biosystems, cat no. KK5515). Beads were emulsified using QX100 droplet generator and Pico-Surf™-1 emulsion oil (Dolomite Microfluidics, cat no. 3200211) as described in example 2.1. The emulsions were transferred to 0.2 ml PCR tubes and a PCR reaction was carried out in a PCR thermocycler (Peqlab, peqSTAR 2× Thermocycler, cat no. 95-07002) using the following temperature cycles:

| | | |
|---|---|---|
| 95° C. | 3 min | |
| | 5 cycles | |
| 95° C. | 15 sec (ramp 1° C. per sec) | |
| 62° C. | 15 sec (ramp 1° C. per sec) | |
| 72° C. | 15 sec (ramp 1° C. per sec) | |
| | 30 cycles | |
| 95° C. | 15 sec (ramp 0.5° C. per sec) | |
| 57° C. | 15 sec (ramp 0.5° C. per sec) | |
| 72° C. | 15 sec (ramp 0.5° C. per sec) | |
| | 1 cycle | |
| 72° C. | 10' | |
| 8° C. | ∞ | |

After the PCR reaction was completed, emulsions were broken by addition of 20 µl TE buffer and 70 µl chloroform and vortexing. Samples were cleared in a centrifugation step at 14,000 rcf for 2 minutes and the upper phases of each sample were removed to a fresh tube. DNA loading buffer was added and the samples were analysed in a preparative 1.2% agarose gel. A band at the size of the linked product at app. 1100 bp was visible (compare FIG. 6, $1^{st}$ PCR). The band was excised and the DNA was purified from the gel using Qiagen MinElute gel extraction kit (cat no. 28604) according to the manufacturer's instructions.

2.3. Nested PCR

The purified linked PCR product obtained in example 2.2 was used as template for a PCR reaction using a second set of antibody VH and VL specific primers. The PCR reaction mix contained the following ingredients in a 25 µl reaction volume: 2 µl template DNA, 0.2 mM dNTPs, 1× buffer A, 0.2 µM of each JH primer (JH1, JH2, JH3, JH4), 0.4 µM Ck2, 0.25% w/v BSA, 1× buffer A and 1 U KAPA Robust Hotstart Polymerase (Kapa Biosystems, cat no. KK5515). The reaction was carried out with the cycling program as described in example 2. The obtained PCR fragments were analysed by 1.2% agarose gel and only one single band at the expected size of 1070 bp was observed (see FIG. 6, $2^{nd}$ PCR). This PCR fragment represents the linked IgH+IgL antibody fragments ready for cloning.

Primers for oePCR according to Meijer et al. (2006)

```
VH4
tattcccatggcgcgccSAGGTGCAGCTGGTGGAG

CH
GACSGATGGGCCCTTGGTGG

VK2
ggcgcgccatgggaatagctagccGATGTTGTGATGACTCAGTCT

CK1
atatatatgcggccgcTTAACACTCTCCCCTGTTGAA

JH1
ggaggcgctcGAGACGGTGACCAGGGTGCC

JH2
ggaggcgctcGAGACGGTGACCATTGTCCC

JH3
ggaggcgctcGAGACGGTGACCAGGGTTCC

JH4
ggaggcgctcGAGACGGTGACCGTGGTCCC

CK2
accgcctccaccggcggccgcttaTTAACACTCTCCCCTGTTGAA

GCTCTT
```

3. Linkage and Amplification of IgVH+IgVL from NLR Encapsulated Single B-Cells

In this step, single oligo dT-Dynabeads that had each captured the immunoglobulin heavy- and light chain mRNA of a single B-cell were used to synthesize cDNA as template for a subsequent PCR reaction. This cDNA remains covalently attached to the beads, thus, the correct immunoglobulin heavy- and light chain pairing as it occurred in the single cell is maintained on the oligo dT Dynabead. In a subsequent steps the oligo dT Dynabeads were emulsified and used in immunoglobulin (H+L)-overlap extension PCR (Ig-oePCR) to physically link the immunoglobulin heavy- and light chain in a consecutive polynucleotide chain.

3.1 Emulsion PCR of Single Matrix Beads in Combination with PCR Primers and Polymerase Emulsion PCR using cDNA-conjugated Dynabeads was carried out according to the procedures set out by the Droplet Digital™ PCR system. Briefly, cDNA-conjugated Dynabeads and primer mixes were mixed with dNTPs, buffer and PCR enzyme provided by the kit and prepared for droplet generation in the QX200™/QX100™ Droplet Digital™ PCR system according to the manufacturer's description. Samples were used to generate emulsion droplets, and subsequently emulsion PCR was performed. Amplified products were recovered after removing oil and dissolving droplets in tris-EDTA and chloroform as described by protocol (Droplet Digital™ PCR system).

3.2 PCR Protocol A

Amplification of linked immunoglobulin variable heavy- and light regions from oligo dT-Dynabead-bound cDNA was performed by emulsion PCR using an established PCR primer system (Meijer et al. 2006) in a two step PCR protocol resulting in a head to head assembly of the two immunoglobulin chains connected via a linker sequence. This linker sequence contained restriction sites for the later insertion of a bi-directional promoter.

3.3 PCR Protocol B

As an alternative, for the linkage of immunoglobulin heavy- and light chains a PCR primer system resulting in a "tail to head" orientation of V-heavy and V-light regions was used (for details see FIG. 2). The immunoglobulin-specific primers were derived from Wardemann et al. (2003), the content of which is expressly enclosed herewith. An overview sketch of this approach is depicted in FIG. 2. FIG. 3 shows an example for such an Ig-variable PCR.

4. Generation of Antibody Expression Library

PCR fragments of linked IgH and IgL cassettes are cloned in bulk into an acceptor plasmid vector using the appropriate restriction sites (NotI/XhoI for PCR protocol A, and BSSHII and BsiWI for PCR protocol B). The conversion of this acceptor to a vector providing all elements required for the expression of full length immunoglobulin heavy- and light chains is described in FIG. 4.

From this acceptor plasmid vector the immunoglobulin expression cassette is lifted via the restriction sites PmeI and PacI into a lentivector transfer vector. This vector provides a mammalian promoter (CMV) and an internal ribosomal entry site followed by the marker gene EGFP. The resulting tri-cistronic antibody expression plasmid is used as lentivector transfer vector (Dull et al., 1998) for the generation of infectious lentivector particles that are used to transfect mammalian cells converting them to antibody expressing cells.

Restriction-free and ligation-less cloning techniques can also be used for library cloning. These prevent the danger seen with restriction that gene constructs are cut at undesireable places resulting in expression of truncated proteins. (e.g. see Gibson D G, Young L, Chuang R Y, Venter J C, Hutchison C A 3rd, Smith H O. (2009). "Enzymatic assembly of DNA molecules up to several hundred kilobases". Nature Methods 6(5): 343-345.doi:10.1038/nmeth.1318. PMID19363495.

5. Expression 5.1 Generation of Lentivector Particles for the Transduction of Expressor Cells Lentivector particles were generated using the so-called third generation lentivector packaging system according to the procedures described in Dull et al. (1998)

5.2 Transduction of Expressor Cells

Standard CHO K1 cells were transduced with lentivectors as described in Dull et al. (1998). To ensure that only one lentivector particle per CHO cell was transduced the multiplicity of infection was adjusted to 0.5 lentivector particles per cell. This resulted in ≥10% of cells being transfected as monitored using the marker gene GFP.

5.3 Encapsulation of Single Expressor Cells in NLR/Highly Parallelized Clonal Expansion CHO cells transfected with the tri-cistronic antibody expression plasmid, using expression of the marker gene (GFP) for positive selection with a cytometer sorter were encapsulated into NLRs at a degree of occupation (DOO) of 0.5. NLRs were cultured in standard culture media resulting in cell proliferation inside the NLR.

4.4 Occupation Control and Growth Harmonization 12 hs after encapsulation, the NLR culture are subjected to Biosorter large particle sorting to positively select all NLR that contain a single living cell that is also positive for GFP fluorescence. By this, non-occupied, empty NLR and those NLR that contain a number of cells that may be caused by aberrant growth rate (e.g., the cell number exceeds the average of that of other NLR by a factor of 1.5) are removed.

4.5 Parallelized Clonal Culture of Recombinant Antibody Producing Cells and Screening for the Identification of Monoclonal Antibodies NLR containing single antibody producing cells are cultured in standard culture medium, and immunoglobulin produced by the growing cell clones is detectable (i) inside the NLR, e.g. using fluorescently labelled probe antigen and (ii) in the culture supernatant fluid surrounding the NLR, e.g., using standard methods such as Western blot, ELISA, immunohistochemistry or functional assays.

The concentration of immunoglobulins inside the NLRs reaches their peak levels faster than that in the supernatant fluid. This temporal retention of immunoglobulin is exploited for screening using a washing step to dilute the immunoglobulin concentration in the supernatant fluid surrounding the NLR prior to intra-NLR-detection of antibody specificity. NLR that stain positive for a fluorescently labelled antigen are then sorted and either left intact, e.g., for an additional confirmatory screening, or disrupted to allow further growth of the antigen-reactive/specific cell clone and the production of monoclonal antibody.

As an alternative to the intra-NLR-detection of antibody specificity the supernatant fluid of expressor cells is assayed for the presence of antibodies of interest. This method allows the assaying for more complex properties of the antibodies of interest such as bioactivity, staining of tissue sections etc.

For this, the supernatant fluid surrounding the NLR obtained after sedimentation or centrifugation of the NLR culture is directly tested for the presence of antibodies with the desired function or other property.

Upon serial fractionation and re-testing of the fractions, single NLRs containing the cell that produced an antibody clone of interest are identified. For this fractionation, standard cell culture recipients down to the microtiter format are used. Supernatants are harvested after a culture period of up to 24 h. NLR containing monoclonal producer cells are obtained in a final step by single-NLR-deposition into microtiter templates (96 well-384 well format) and harvesting of supernatant and testing is performed after an extended culture period of 72 h.

5. Expression and Library Screening for the Retrieval of a Clonal Cell Line Expressing an Antibody of Interest.

AB2 expressor cells representing the antibody of interest were encapsulated as single cells in NLRs and 30 NLRs were added (spiked) to a culture of 210,000 NLRs containing expressor cells expressing an irrelevant antibody. This bulk NLR culture, representing the library of expressor cells was cultured in complete culture medium (See FIG. 6).

Subsequently, the 210,030 NLR were fractionated by pipetting the culture into 96 wells of a microtiter plate (1st fractionation of culture). This culture was kept for 3 days to allow for cell growth, antibody expression and secretion of antibodies into the supernatant fluid outside the NLR.

At day four 50 ul of the culture supernatant of each of the 96 wells was screened for the presence of AB2-antigen specific antibodies by ELISA. Positive cultures were identified as depicted in Figure E2. One exemplary positive NLR culture (Bh5) was selected for clone identification by placement of single NLRs of culture Bh5 into microtiter plates followed by a second ELISA screen another 3 days later.

This led to the identification of a single NLR in well E4, representing a clonal cell line expressing mAB H5/E4 specific to AB2-antigen (see FIG. 7B).

6. List of Equipment and Materials Used

Biosorter large particle flow cytometer, Union Biometrica, Geel, Belgium

Nisco laminar jet break-up encapsulator, Nisco Engineering AG, Zurich, Switzerland QX100/200 droplet generator, Bio-Rad, Cressier, Switzerland Alginate, Pronova, Norway Dynabeads mRNA DIRECT Micro Kit; Life Technologies, Basel, Switzerland Encapsulation buffer: 0.9% NaCl (w/v); 2.2 mM HEPES pH 7.4
Encapsulation buffer: (0.9% NaCl (w/v); 2.2 mM HEPES pH 7.4)
Hardening solution: 100 mM $CaCl_2$), 13 mM HEPES pH 7.4
NLR dissolution reagent: 100 mM EDTA
Cell lysis buffer/NLR (100 mM Tris-HCl, pH 7.5; 500 mM LiCl; 5 mM Dithiothreitol; 0.1% Lauroylsarcosine; 0.1% Tween20; 0.1% Deoxycholate)
Immunoglobulin-specific SmartFlare RNA Detection Probes, Millipore, Zug, Switzerland
Maxima RT, Thermo Scientific, Reinach, Switzerland
Primers for oePCR: according to Meijers et al. (2006) or Wardemann, et al. (2003), Microsynth, Balgach, Switzerland.
5-Propargylamino-dCTP-Cy5, Jena Bioscience GmbH Jena, Germany
dNTPs, Thermo Scientific, Reinach, Switzerland.
ddPCR supermix, Bio Rad, Cressier Switzerland
Droplet generator oil, Bio Rad, Cressier Switzerland
Molecular cloning in plasmid vectors acc. to standard methods
Emulsion droplet Cell lysis buffer: 50 mM Tris-HCl pH 8.3, 50 mM KCl, 50 mM LiCl, 5 mM EDTA, 10 mM DTT, 0.2 mg/ml Proteinase K
RiboLock RNase Inhibitor #EO0381, Thermo Scientific, Fischer, Reinach, Switzerland
KAPA Robust Hotstart DNA Polymerase, KAPA Biosystems, KE5506, Axon lab, Baden, Switzerland.
dNTPs, NEB, Bioconcept, Allschwil, Switzerland
10% w/v Pluronic F68 #A1288,0100 in water, Applichem, Axon lab Baden, Switzerland.
Pico-Surf 1, 2% in Novec 7500 (#3200211, Lot 211014, Dolomite, Valve Technology AG, Guettingen, Switzerland
Pico-Surf 2, 2% in Novec 7500 (#3100281, Lot 091014, Dolomite)
peqSTAR 2× Thermocycler, Peqlab, #95-07002
Agarose, ultrapure, Invitrogen #15510-027
peqGREEN dye, Peqlab #37-5010, use at 1:20,000
1 kb DNA Ladder, NEB, Bioconcept, Allschwil, Switzerland #N3232S
Culture medium CHO-K1: Ham's F12 incl. 2 mM Glutamin, 10% FBS, Invitrogen, Zug, Switzerland.
Peptide antigens used for ELISA (AB2-antigen protein sequence: stgdadgpggpgipdgpggn; irrelevant control peptide protein sequence: lpttmnyplwsqsyedssnq) 1 mg scale not purified, Peptides&Elephants GmbH, Potsdam, Germany
ELISA plates: EIA/RIA plate, 96 well half area plate, flat bottom (Costar, Corning)
Coating Buffer: 15 mM $Na_2CO_3$, 30 mM $NaHCO_3$, pH 9.6
Wash Buffer: PBS with 0.05% Tween
Blocking Solution: 2% BSA in PBS
2nd Antibody: Goat α-human IgG Fc-Specific (Jackson Immuno, #109-035-098), 1:4000 diluted in 0.5% BSA/PBS
Detection solution: TMB (Sigma, #T2285) 1:20 diluted in 30 mM Citric Acid, pH 4.1 (Sigma, #C2402)
1M $H_2SO_4$ (AppliChem, #A2699)

Microreactors (also called "NanoLiter Reactors" or "NLR" herein, although these reactors can also have picoliter volumes) of a single cell (C, surrogate B-cell expressing antibody and marker gene GFP for better visibility is shown here) with mRNA capture matrix Dynabeads (DB). Surrogate B cells were generated by stable transduction of CHO-K1 cells with lentivectors bearing an attenuated bi-cistronic human IgG expression cassette leading to low IgG expression levels to match Ig-expression in original human memory B cells. Attenuation was achieved by positioning of the bi-cistronic antibody expression cassette behind the stop codon of the CMV-promoter-EGFP cassette. Surrogate B cells, as used herein faithfully reflect the behavior of B cells, or T-cells.

Figure 1:
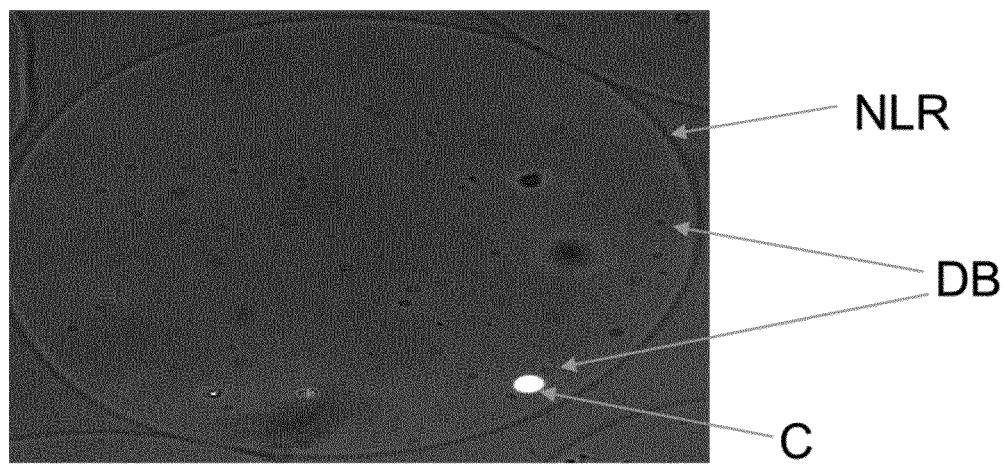
FIG. 1: Microphotograph of co-encapsulation in Microreactors
Figure 2:
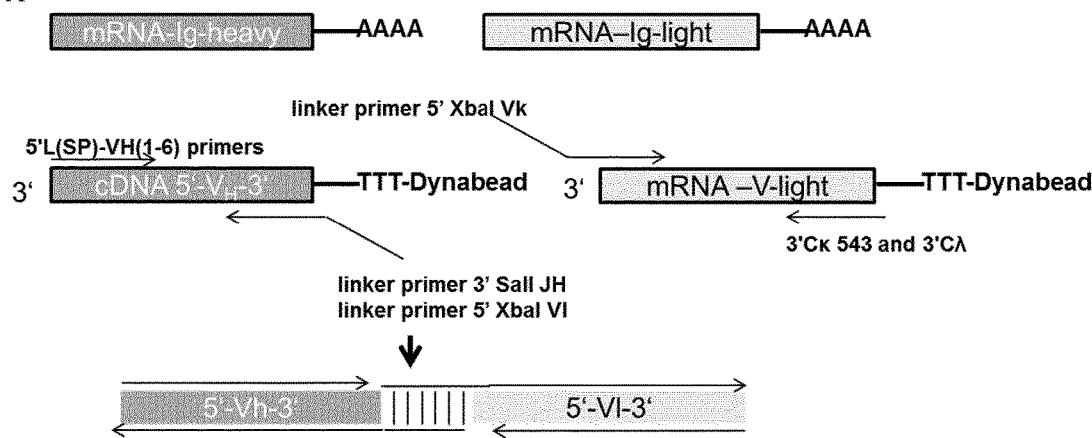
Figure 2:
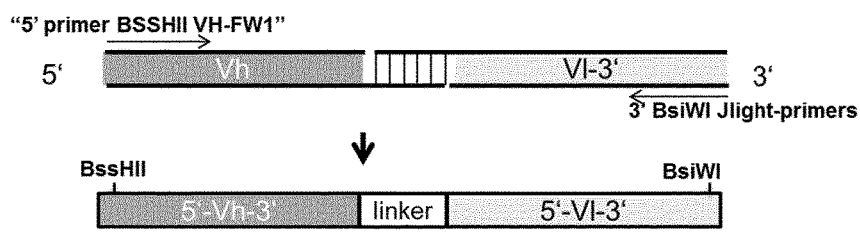

FIG. 2: Schematic overview on immunoglobulin v-region PCR strategy $1^{st}$ PCR: Overlap extension PCR (oePCR) for amplification and linkage of immunoglobulin variable heavy and light chains in a "tail to head" orientation of V-heavy and V-light regions. Linker primers for OE PCR were of the following configuration.

Ig-variable heavy chain: linker primer 3' SalI JH: tat-tcgcactgcgcggcGTCGACgc-(JH family specific sequences)

Ig-variable kappa light chain: linker primer 5' XbaI Vk: gccgcgcagtgcgaataTCTAGAtgt-(FW1-V-kappa family specific sequences), linker primer 5' XbaI Vl: gccgcgcagtgcgaataTCTAGAtgt-(FW1-V-lambda family specific sequences).

Additional primers used were 5'L(SP)-VH(1-6) primers, and 3'Cκ 543 and 3'Cλ. Capital letters indicate the restriction sites used for insertion of the polynucleotide cassette providing the constant part of IgH, a cleavage site for later proteolytic cleavage and a signal peptide for secretion of IgKappa/lambda in a later cloning step (see below). Small letters indicate the linker sequences used in overlap extension PCR to link heavy- and light chain constructs.

$2^{nd}$ PCR: Nested PCR (nPCR) was carried out for further amplification and insertion of restriction sites into the PCR product via the primers in order to facilitate cloning in expression vectors.

5' primers containing the BSSHII restriction site (capital letters) were used according to this configuration:

5' primer BSSHII VH-FW1: attttttttGCGCGCtgt-(FW1-V-heavy family specific sequences); 3' primers: the 3' BsiWI Jκ-primers as published in Wardemann et al. (2003) were used.

Figure 3:
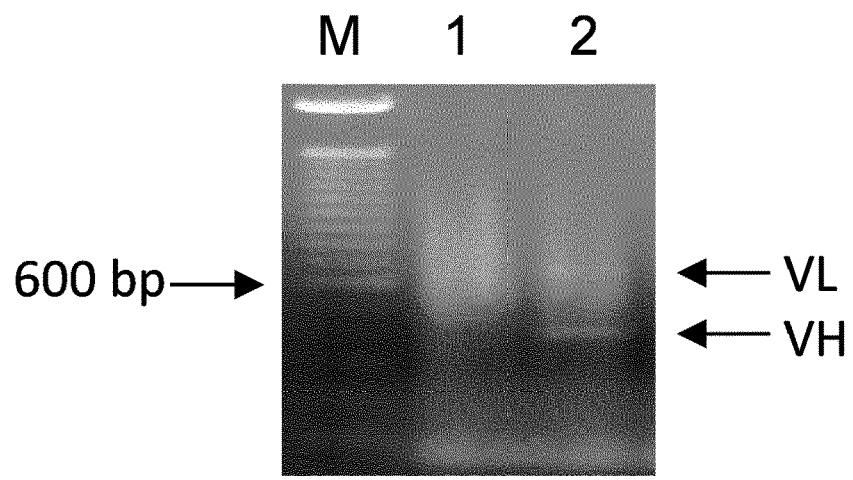
Figure 3:
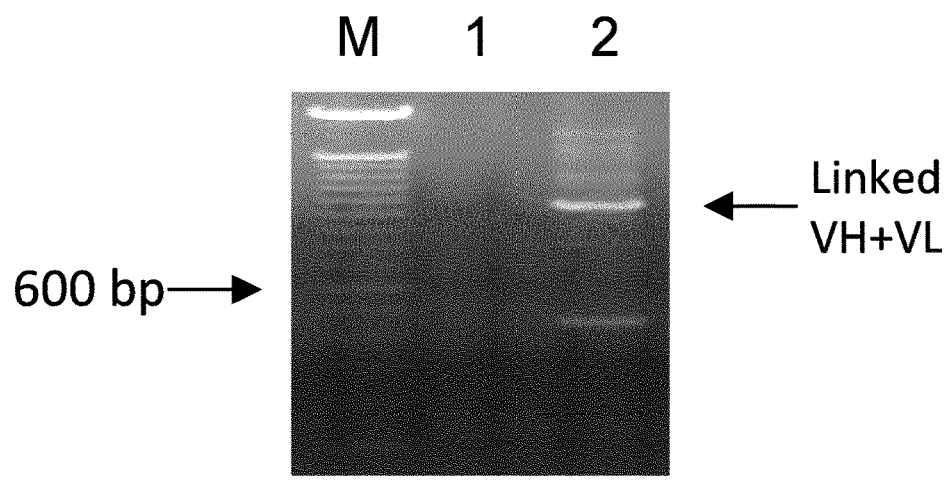

FIG. 3: Amplification of linked immunoglobulin variable heavy- and light chains from encapsulated (single) antibody-expressing cells.

A two step PCR protocol was used to amplify variable heavy- and light chains derived from a single cell via solid matrix-bound cDNA (oligo dT Dynabeads).

(A) 1st PCR amplification of variable region of heavy and light chains followed by overlap extension in single tube/one step reaction on cDNA bound by oligo dT Dynabeads (lane 2). As control the same procedure was carried out using cells not expressing an antibody (lane 1).

(B) 2nd (nested) PCR on 1st-round-PCR products showing the presence of a linked immunoglobulin heavy- and light chain derived from antibody expressing cells (lane 2) but not from control cells (lane 1).

Figure 4:
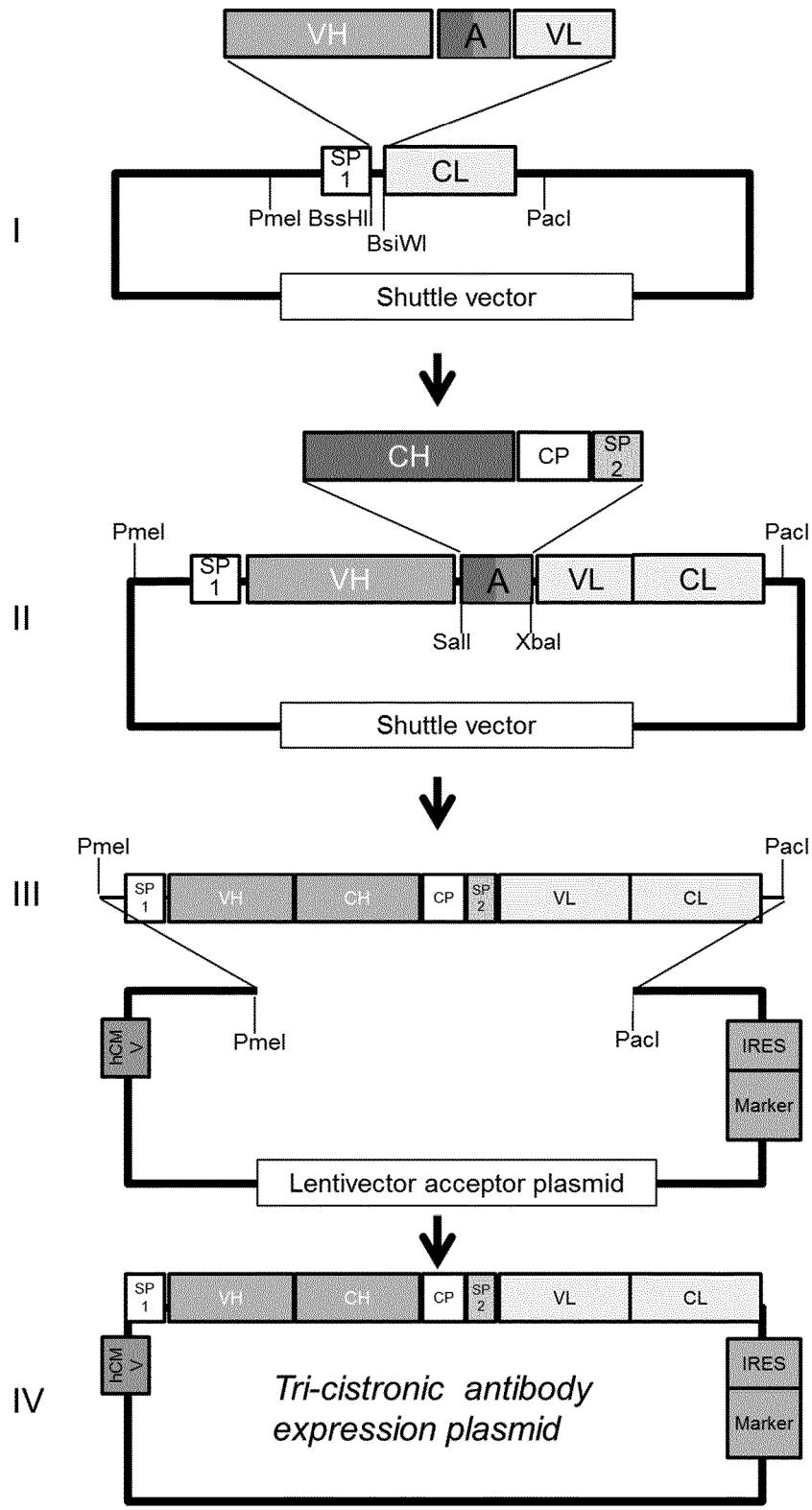

FIG. 4: Schematic overview on cloning steps to generate the Tri-cistronic antibody expression plasmid.
   I. Linked IgVH+IgVL PCR product is inserted into a shuttle vector providing the immunoglobulin signal peptide and the constant region of Ig kappa/lambda.
   II. A polynucleotide cassette providing the constant part of IgH, a cleavage site for later proteolytic cleavage and a signal peptide for secretion of Ig kappa/lambda is inserted by molecular cloning.
   III. The resulting bi-cistronic expression cassette is shuttled into a lentivector transfer vector by molecular cloning to yield the final Tri-cistronic expression vector used to generate lentivector particles.

Figure 5:
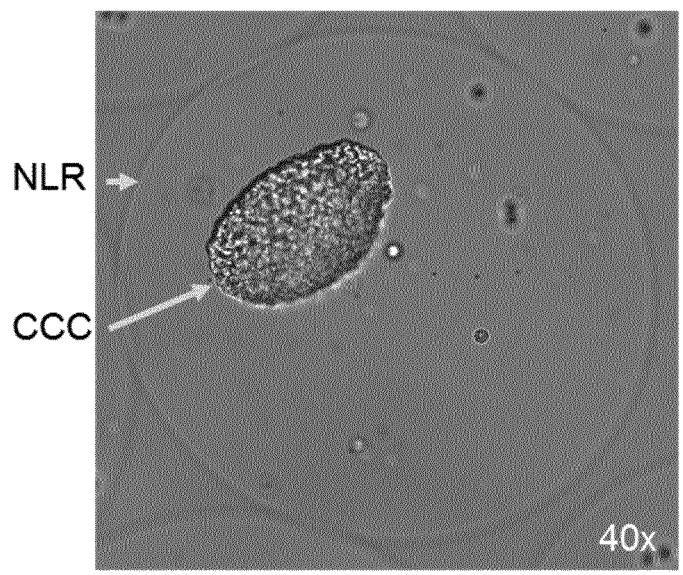
Figure 5:
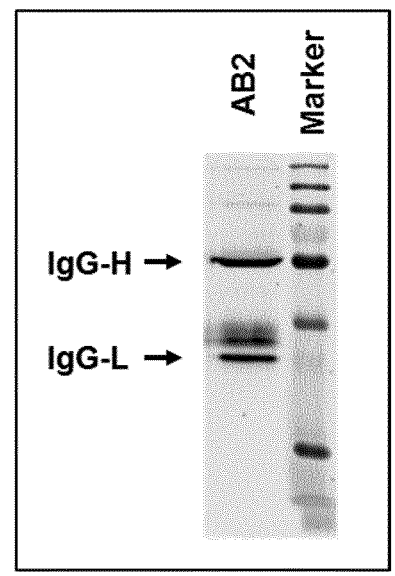

FIG. 5: Clonal propagation of expressor cells in nanoliter reactors and detection of antibody production.
   A) Clonal cell cluster (CCC) arising from a single CHO expressor cell eight days after encapsulation in a nanoliter reactor (NLR). The cell was transformed by a lentivector particle encoding the tri-cistronic antibody-EGFP-expression cassette prior to encapsulation.
   B) Production of antibody (full IgG) by clonal cell cluster (clone AB2). Western blot of Prot G purified antibody recovered from fluid inside NLR. PAGE was run under reducing conditions showing expression of Ig-heavy- and Ig-light chain.

Figure 6:
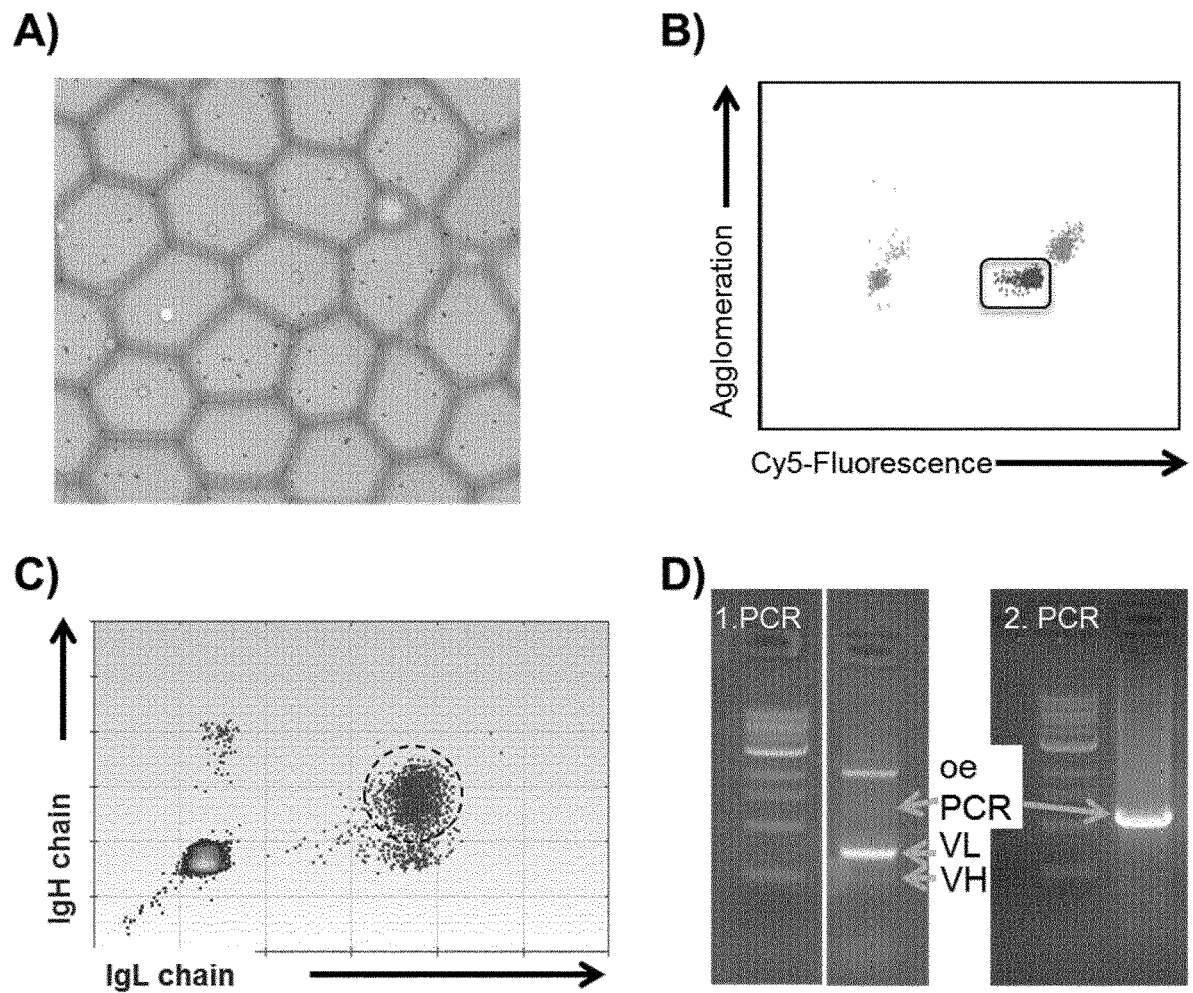

FIG. 6: High throughput single-cell RT-PCR of immunoglobulin heavy and light chain mRNA.
   A) Droplets containing antibody expressing cells and mRNA capture beads before cell lysis (Step 1: cell encapsulation). Cells and oligo-dT Dynabeads in lysis buffer were encapsulated in Pico-Surf 2 emulsion oil, volume per droplet is approximately 1 nl, picture was taken directly after encapsulation and before cell lysis.
   B) Fluorescence activated sorting of singlet cDNA loaded capturing beads upstream of digital droplet PCR. Square gate defines singlet bead population.
   C) Single bead digital droplet PCR reveals the presence of a major population of capture beads containing both IgH and IgL, amplified sequences (dotted circle). Presence of IgH and IgL cDNA is monitored by release of a quenched fluorophore specific for either Ig chain by the PCR reaction (IgH=Y axis, IgL=X axis). Droplet PCR was analyzed using the QX100 droplet analyzer.
   D) Overlap extension PCR demonstrating the generation of linked IgH and IgL derived from single mRNA capturing beads. 1st PCR performed in emulsion droplets and second (nested) PCR performed in bulk.

Figure 7:
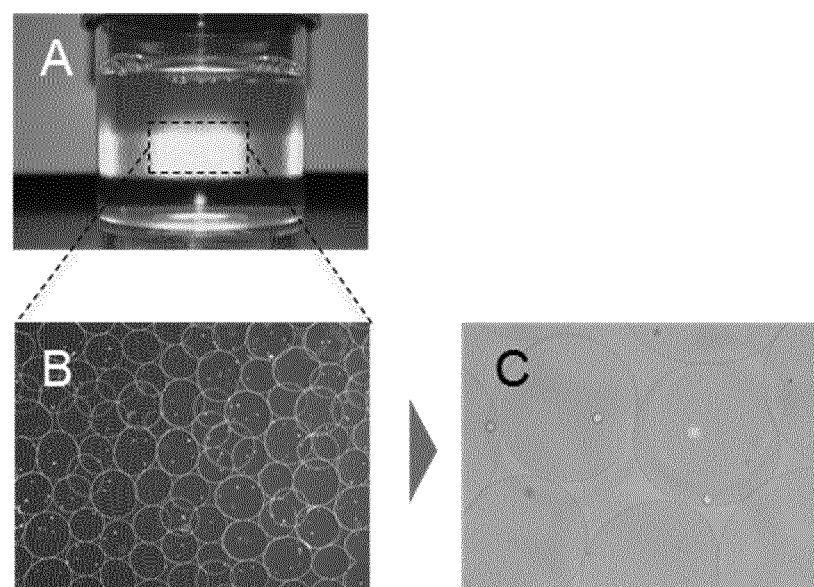

FIG. 7: Propagation of a NLR culture representing the library of antibody expressor cells
   A) Photo of NLR culture composed of single encapsulated expressor cells.
   B) Photo micrograph of a section of the bulk NLR culture at day 1.
   C) Fluorescent photo micrograph of NLR taken at day 4 of culture showing GFP positive clonal cell clusters (arrows) growing inside the NLRs that were the result of clonal expansion of a single encapsulated expressor cell.

Figure 8:
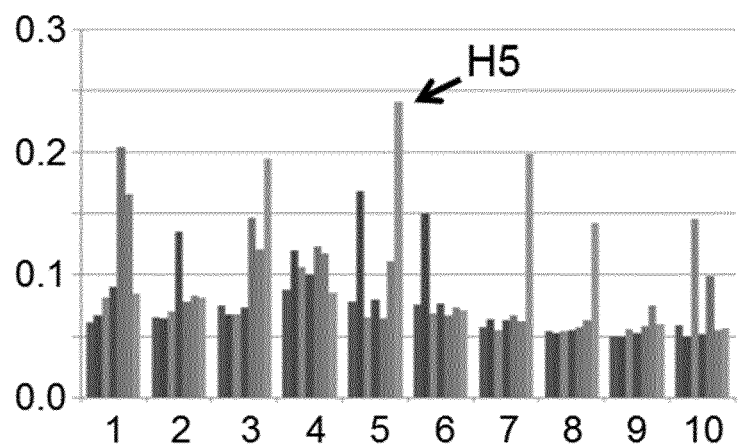
Figure 8:
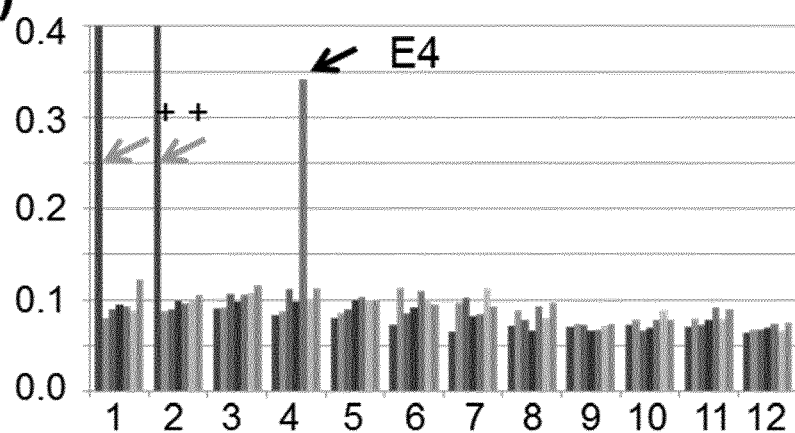

FIG. 8: Identification and isolation of a clonal cell line expressing a mAb of interest.
   A) 30 NLR bearing AB2 expressor cells were mixed to a more than 300 fold excess of NLRs bearing irrelevant expressor cells and bulk culture was plated in 80 wells of a 96 well plate. 4 days after encapsulation and plating the supernatant fluid of the NLR cultures was assayed by AB2-antigen-specific ELISA and AB2 positive culture wells were detected. Culture H5 was selected for cloning (arrow).
   B) NLR singularization and identification of clonal cell line E4. Single NLRs from bulk culture H5 were placed in individual culture wells. After 3 days, the supernatant fluid was assayed by AB2-ELISA and well E4 was identified demonstrating isolation of a clonal cell line that expressed an AB2-specific monoclonal antibody. Positive controls (+) were run in wells A1 and A2.

REFERENCES

Embleton et al., Nucleic Acids Research, Vol. 20, No. 15, 3831 (1992)
Wardemann, et al., Science 301, 1374 (2003)
Boulianne et al., Nature 312, 643-646, (1984)
Morrisson et al., PNAS 82, 6851-6855 (1984)
Card et al., Cancer Immunol Immunother. April; 53(4):345-57 (2004)
Szymczak et al., Nat Biotechnol 22:589-594 (2004)
Serp et al., Biotechnology and Bioengineering, Vol. 70 (1) (2000)
Gomez-Herreros et al., Nucleic Acids Research, 40, 6508-6519 (2012)
Martinez et al. Macromol. Biosciences, 12, 946-951 (2012)
Prüße et al., Chem. Eng Technol. 1998, 21(1):29-33
McHeyzer-Williams and Ahmed, Curr. Opin. Immunol. 11, 172-179, (1999)
Bernasconi et al., Science 298, 2199-202 (2002)
Meijer et al., J Mol Biol. 358: 764-772 (2006)
Dull et al., J. Virol 72(11) (1998)
Diehl et al. Nature Methods, 3, 551-559 (2006)

Primers Used

First PCR:

Ig-Variable Heavy Chain:

```
Forward primers:
1. 5' SP-VH1 ACAGGTGCCCACTCCCAGGTGCAG 2. 5' SP-VH3 AAGGTGTCCAGTGTGARGTGCAG 3. 5' SP-VH4/6 CCCAGATGGGTCCTGTCCCAGGTGCAG 4. 5' SP-VH5 CAAGGAGTCTGTTCCGAGGTGCAG Reverse primer:
5. 3'CHg1 adaptor-GTTGTCCACCTTGGTGTTGCTGG 6. 3' Cμ CH1 adaptor-GGGAATTCTCAGAGGAGACGA
```

Ig-Variable Kappa Chain:

```
Forward primers:
7. 5' SP Vκ1/2
reverseadaptor-ATGAGGSTCCCYGCTCAGCTGCTGG 8. 5' SP Vκ3
reverseadaptor-CTCTTCCTCCTGCTACTCTGGCTCCCAG 9. 5' SP Vκ4
reverseadaptor-ATTTCTCTGTTGCTCTGGATCTCTG Reverse primer:
10. 3' Cκ 543 GTTTCTCGTAGTCTGCTTTGCTCA
```

Ig-Variable Lambda Chain:

```
Forward primers:
11. 5' SP Vλ1
reverseadaptor-GGTCCTGGGCCCAGTCTGTGCTG 12. 5' SP Vλ2
reverseadaptor-GGTCCTGGGCCCAGTCTGCCCTG 13. 5' SP Vλ3
reverseadaptor-GCTCTGTGACCTCCTATGAGCTG 14. 5' SP Vλ4/5
reverseadaptor-GGTCTCTCTCSCAGCYTGTGCTG 15. 5' SP Vλ6
reverseadaptor-GTTCTTGGGCCAATTTTATGCTG 16. 5' SP Vλ7
reverseadaptor-GGTCCAATTCYCAGGCTGTGGTG 17. 5' SP Vλ8
reverseadaptor-GAGTGGATTCTCAGACTGTGGTG Reverse primer:
18. 3' Cλ CACCAGTGTGGCCTTGTTGGCTTG
```

Overlap Extension PCR:

```
Forward primers:
19. 5' BSSH2 VH1/5
CTGCAGCGCGCGTACAT TCCGAGGTGCAGCTGGTGCAG 20. 5' BSSH2 VH3
CTGCAGCGCGCGTACATTCTGAGGTGCAGCTGGTGGAG 21. 5' BSSH2 VH4
CTGCAGCGCGCGTACATTCCCAGGTGCAGCTGCAGGAG 22. 5' BSSH2 VH3-23
CTGCAGCGCGCGTACATTCTGAGGTGCAGCTGTTGGAG 23. 5' BSSH2 VH4-34
CTGCAGCGCGCGTACATTCCCAGGTGCAGCTACAGCAGTG Reverse primers:
24. 3'BsiWI Jκ1/2/4
GCCACCGTACGTTTGATYTCCACCTTGGTC 25. 3'BsiWI Jκ3
GCCACCGTACGTTTGATATCCACTTTGGTC 26. 3'XhoICλ CTCCTCACTCGAGGGYGGGAACAGAGTG
``` oePCR Linker Primers

```
Ig-variable heavy chain:
28. 3' SalI JH
tattcgcactgcgcggcGTCGACgc-
(JH family specific sequences)

Ig-variable light chain:
29. 5' XbaI Vk
gccgcgcagtgcgaataTCTAGAtgt-
(FW1-V-kappa family specific sequences)

30. 5' XbaI Vl
gccgcgcagtgcgaataTCTAGAtgt-
(FW1-V-lambda family specific sequences)
``` nPCR
5' Primers:

```
BSSHII VH-FW1
attttttttGCGCGCtgt-
(FW1-V-heavy family specific sequences
```

3' Primers
3' BsiWI Jκ-Primers (See Table Below)
Restriction sites are shown in bold.

TABLE 1 further primers to be used to carry out the invention.

| IgH | | Sense | | Antisense |
|---|---|---|---|---|
| First PCR | 5' L-VH1 | ACAGGTGCCCACTCCCAGGTGCAG | 3' Cµ CH1 | GGGAATTCTCAGAGGAGACGA |
| | 5' L-VH3 | AAGGTGTCCAGTGTGARGTGCAG | | |
| | 5' L-VH4/6 | CCCAGATGGGTCCTGTCCCAGGTGCAG | | |
| | 5' L-VH5 | CAAGGAGTCTGTTCCGAGGTGCAG | | |
| Second PCR | 5' AgeI VH1/5 | CTGCAACCGGTGTACAT TCCGAGGTG CAGCTGGTGCAG | 3' SalI JH1/2 | TGCGAAGTCGACGCCTGAGGAGACGGTGAC CAG |
| | 5' AgeI VH3 | CTGCAACCGGTGTACATTCTGAGGTGC AGCTGGTGGAG | 3' SalI JH3 | TGCGAAGTCGACGCTGAAGAGACGGTGACC ATTG |
| | 5' AgeI VH4 | CTGCAACCGGTGTACATTCCCAGGTGC AGCTGCAGGAG | 3' SalI JH4/5 | TGCGAAGTCGACGCTGAGGAGACGTGACCA G |
| | 5' AgeI VH3-23 | CTGCAACCGGTGTACATTCTGAGGTGC AGCTGTTGGAG | 3' SalI JH6 | TGCGAAGTCGACGCTGAGGAGACGGTGACC GTG |
| | 5' AgeI VH4-34 | CTGCAACCGGTGTACATTCCCAGGTGC AGCTACAGCAGTG | | |

| Igλ | | Sense | | Antisense |
|---|---|---|---|---|
| First PCR | 5' L Vλ1 | GGTCCTGGGCCCAGTCTGTGCTG | 3' Cλ | CACCAGTGTGGCCTTGTTGGCTTG |
| | 5' L Vλ2 | GGTCCTGGGCCCAGTCTGCCCTG | | |
| | 5' L Vλ3 | GCTCTGTGACCTCCTATGAGCTG | | |
| | 5' L Vλ4/5 | GGTCTCTCTCSCAGCYTGTGCTG | | |
| | 5' L Vλ6 | GTTCTTGGGCCAATTTTATGCTG | | |
| | 5' L Vλ7 | GGTCCAATTCYCAGGCTGTGGTG | | |
| | 5' L Vλ8 | GAGTGGATTCTCAGACTGTGGTG | | |

TABLE 1-continued further primers to be used to carry out the invention.

| | | | | | | |
|---|---|---|---|---|---|---|
| Second PCR | 5' AgeI Vλ1 | CTGCTACCGGTTCCTGGGCCCAGTCTG TGCTGACKCAG | 3' XhoI Cλ | | CTCCTCACTCGAGGGYGGGAACAGAGTG | |
| | 5' AgeI Vλ2 | CTGCTACCGGTTCCTGGGCCCAGTCTG CCCTGACTCAG | | | | |
| | 5' AgeI Vλ3 | CTGCTACCGGTTCTGTGACCTCCTATG AGCTGACWCAG | | | | |
| | 5' AgeI Vλ4/5 | CTGCTACCGGTTCTCTCTCSCAGCYTG TGCTGACTCA | | | | |
| | 5' AgeI Vλ6 | CTGCTACCGGTTCTTGGGCCAATTTTA TGCTGACTCAG | | | | |
| | 5' AgeI Vλ7/8 | CTGCTACCGGTTCCAATTCYCAGRCTG TGGTGACYCAG | | | | |

| Igκ | | Sense | | | Antisense | |
|---|---|---|---|---|---|---|
| First PCR | 5' L Vκ1/2 | ATGAGGSTCCCYGCTCAGCTGCTGG | 3' Cκ 543 | | GTTTCTCGTAGTCTGCTTTGCTCA | |
| | 5' L Vκ3 | CTCTTCCTCCTGCTACTCTGGCTCC CAG | | | | |
| | 5' L Vκ4 | ATTTCTCTGTTGCTCTGGATCTCTG | | | | |
| Second PCR | 5' Pan Vκ | ATGACCCAGWCTCCABYCWCCCTG | 3' Cκ 494 | | GTGCTGTCCTTGCTGTCCTGCTC | |
| Specific PCR | 5' AgeI Vκ 1-5 | CTGCAACCGGTGTACATTCTGACATCC AGATGACCCAGTC | 3' BsiWI Jκ1/2/4 | | GCCACCGTACGTTTGATYTCCACCTTGGTC | |
| | 5' AgeI Vκ 1-9 | TTGTGCTGCAACCGGTGTACATTCAGA CATCCAGTTGACCCAGTCT | 3' BsiWI Jκ3 | | GCCACCGTACGTTTGATATCCACTTTGGTC | |
| | 5' AgeI Vκ 1D-43 | CTGCAACCGGTGTACATTGTGCCATCC GGATGACCCAGTC | 3' BsiWI Jκ5 | | GCCACCGTACGTTTAATCTCCAGTCGTGTC | |
| | 5' AgeI Vκ 2-24 | CTGCAACCGGTGTACATGGGGATATTG TGATGACCCAGAC | | | | |
| | 5' AgeI Vκ 2-28 | CTGCAACCGGTGTACATGGGGATATTG TGATGACTCAGTC | | | | |
| | 5' AgeI Vκ 3-11 | TTGTGCTGCAACCGGTGTACATTCAGA AATTC | | | | |
| | 5' AgeI Vκ 3-15 | CTGCAACCGGTGTACATTCAGAAATAG TGATGACGCAGTC | | | | |
| | 5' AgeI Vκ 3-20 | TTGTGCTGCAACCGGTGTACATTCAGA AATTGTGTTGACGCAGTCT | | | | |
| | 5' AgeI Vκ 4-1 | CTGCAACCGGTGTACATTCGGACATCG TGATGACCCAGTC | | | | |

What is claimed is:

1. A method for recovering two or more genes, gene products, or cDNAs, encoding for an immunoreceptor having two or more subunits from a source cell, said method comprising:

a) encapsulating a source cell producing cellular mRNAs together with mRNA capturing moieties in a microreactor having a lumen wherein the mRNA capturing moieties are beads or particles;

b) lysing the source cell in the microreactor, to allow release of the cellular mRNAs in the lumen of the microreactor, and the subsequent attachment thereof to the mRNA capturing moieties generating mRNAs attached to the mRNA capturing moieties;

c) disrupting the microreactor and reverse transcribing the mRNAs attached to the mRNA capturing moieties in solution to obtain corresponding cDNAs;

d) creating a construct from the cDNAs by PCR, which construct encompasses two or more genes, gene products, or cDNAs encoding for the subunits of the immunoreceptor, and e) cloning of the PCR construct into a plasmid vector to obtain a bi- or multicistronic expression vector that encodes for the immunoreceptor.

2. The method according to claim 1, which further comprises, after step c)

(i) monitoring cDNA synthesis by reverse transcription of the mRNAs attached to the mRNA capturing moieties, and (ii) excluding aggregated mRNA capturing moieties.

3. The method according to claim 1, wherein the creation of a construct that encompasses the two or more genes, gene products, or cDNAs encoding for the subunits of the immunoreceptor, as set forth in step d), is accomplished by amplifying the cDNA by overlap extension PCR.

4. The method according to claim 1, wherein the immunoreceptor is an antibody having at least two subunits, or a T-cell receptor having at least two subunits.

5. A method of creating a library of expressor cells, wherein each expressor cell is capable of expressing two or more genes, gene products, or cDNAs encoding for the subunits of the immunoreceptor recovered according to the method of claim 1, which method further comprises:
  g) transfecting the expressor cells with the bi- or multicistronic expression construct, and
  h) encapsulating the expressor cells into microreactors.

6. A method of screening a library of expressor cells produced by the method of claim 5, for one cell that expresses an immunoreceptor that has specificity for a given target molecule, which method comprises at least one of:
  i) use of a labeled target that is capable of entering into the microreactor and binding to an immunoreceptor expressed by the expressor cell comprised therein or
  j) detecting an immunoreceptor expressed by the expressor cell that has escaped from the microreactor into a supernatant in combination with serial fractionation of the microreactor culture.

7. The method according to claim 1, wherein the mRNA capturing moieties are magnetic beads or particles.

8. The method according to claim 1, wherein the bi- or multicistronic expression vector is a 2A peptide-linked multicistronic vector with or without combination with an IRES (internal ribosome entry site) sequence.

9. The method according to claim 1, wherein the microreactor comprises a material selected from the group consisting of:
  (a) hydrogel-forming polymers,
  (b) cellulose derivatives, and
  (c) polysaccharides.

10. The method according to claim 1, wherein the microreactor is formed as aqueous droplet in a water/oil emulsion.

11. The method according to claim 10, wherein the microreactor has a diameter of between about 10 μm and about 1000 μm.

12. The method according to claim 10, wherein the microreactor has a volume of between about 0.52 pl and about 523 nl.

13. The method according to claim 1, wherein the source cell is a mammalian cell selected from the group consisting of immature B cells, mature B-cells, immature T-cells and mature T-cells.

14. The method according to claim 1, wherein the two or more genes, gene products, or cDNAs encoding for the subunits of the immunoreceptor are selected from the group consisting of:
  a) a VDJ rearranged Ig heavy chain gene and a VJ rearranged Ig light chain gene, and
  b) a rearranged TCR alpha chain gene and a rearranged TCR beta chain gene.

15. The method according to claim 1, which further comprises the step of inserting cDNA encoding for
  a) an Ig constant H subdomain and/or Ig constant L subdomain, or
  b) a TCR alpha chain and a TCR beta chain
into the PCR product.

16. The method according to claim 9, wherein the hydrogel-forming polymers are selected from poly(diallyldimethylammonium chloride), poly(ethyleneimine), polylysine, polyacrylamides and acrylic acids.

17. The method according to claim 9, wherein the cellulose derivatives are selected from carboxymethylcellulose and cellulose esters.

18. The method according to claim 9, wherein the polysaccharides are selected from agaroses, alginates, carrageenans, pectinates, and chitosans.

* * * * *